US009956390B2

(12) United States Patent
Rousso et al.

(10) Patent No.: US 9,956,390 B2
(45) Date of Patent: *May 1, 2018

(54) IMPLANTABLE LEAD CONNECTOR

(71) Applicant: Impulse Dynamics NV, Willernstad (AN)

(72) Inventors: Benny Rousso, Rishon-LeZion (IL); Yuval Mika, Closter, NJ (US); Shlomo Ben-Haim, London (GB); Daniel Burkhoff, West Harrison, NY (US); David Prutchi, Voorhees, NJ (US)

(73) Assignee: Impulse Dynamics NV, Willemstad, Curacao (AN)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/136,933

(22) Filed: Apr. 24, 2016

(65) Prior Publication Data
US 2016/0235964 A1    Aug. 18, 2016

Related U.S. Application Data

(63) Continuation of application No. 14/254,945, filed on Apr. 17, 2014, now Pat. No. 9,320,886, which is a (Continued)

(51) Int. Cl.
*A61N 1/378* (2006.01)
*A61N 1/02* (2006.01)
(Continued)

(52) U.S. Cl.
CPC .............. *A61N 1/025* (2013.01); *A61N 1/05* (2013.01); *A61N 1/08* (2013.01); *A61N 1/362* (2013.01);
(Continued)

(58) Field of Classification Search
CPC ............ A61N 1/36125; A61N 1/36128; A61N 1/362; A61N 1/3621; A61N 1/3622;
(Continued)

(56) References Cited

U.S. PATENT DOCUMENTS 5,289,048 A    2/1994   Ishihara et al.
5,314,451 A    5/1994   Mulier
(Continued)

FOREIGN PATENT DOCUMENTS

WO    WO 2007/029254    3/2007
WO    WO 2008/076925    6/2008
(Continued)

OTHER PUBLICATIONS

Applicant-Initiated Interview summary dated Aug. 3, 2015 From the US Patent and Trademark Office Re. U.S. Appl. No. 14/254,945.
(Continued)

*Primary Examiner* — Allen Porter, Jr.

(57) ABSTRACT

An implantable lead connector configured for long term implantation and to electrically interconnect multiple medical devices and to channel electrical signals between said interconnected devices and a target organ, comprising: a first port adapted to receive a first signal suitable to stimulate a target tissue, a second port adapted to receive a second signal suitable to stimulate a target tissue, and a third port configured to connect to a target organ, wherein at least one of said first and second ports is configured to connect to a signal generator not integrated with said connector.

50 Claims, 11 Drawing Sheets

Related U.S. Application Data continuation of application No. 13/265,874, filed as application No. PCT/IB2010/051783 on Apr. 23, 2010, now Pat. No. 8,706,230.

(60) Provisional application No. 61/202,958, filed on Apr. 23, 2009.

(51) Int. Cl.
| | | |
|---|---|---|
| *A61N 1/08* | (2006.01) | |
| *A61N 1/372* | (2006.01) | |
| *A61N 1/375* | (2006.01) | |
| *A61N 1/05* | (2006.01) | |
| *A61N 1/362* | (2006.01) | |
| *A61N 1/39* | (2006.01) | |

(52) U.S. Cl.
CPC ............. *A61N 1/372* (2013.01); *A61N 1/378* (2013.01); *A61N 1/3752* (2013.01); *A61N 1/3785* (2013.01); *A61N 1/3962* (2013.01)

(58) Field of Classification Search
CPC .... A61N 1/368; A61N 1/372; A61N 1/37211; A61N 1/375; A61N 1/3752; A61N 1/38; A61N 1/39
USPC .......................................... 607/5, 9, 14, 37
See application file for complete search history.

(56) References Cited

U.S. PATENT DOCUMENTS

| | | | |
|---|---|---|---|
| 5,411,535 | A | 5/1995 | Fujii et al. |
| 5,755,742 | A | 5/1998 | Schuelke et al. |
| 5,782,892 | A | 7/1998 | Castle et al. |
| 5,999,848 | A | 12/1999 | Gord et al. |
| 6,141,588 | A | 10/2000 | Cox et al. |
| 6,208,896 | B1 | 3/2001 | Mulhauser |
| 6,907,285 | B2 | 6/2005 | Denker et al. |
| 7,647,102 | B2 | 1/2010 | Routh et al. |
| 7,758,384 | B2 | 7/2010 | Alexander et al. |
| 8,706,230 | B2 | 4/2014 | Rousso et al. |
| 2003/0163171 | A1* | 8/2003 | Kast ................ A61N 1/3752 607/36 |
| 2004/0015211 | A1 | 1/2004 | Nurmikko et al. |
| 2004/0034392 | A1 | 2/2004 | Spadgenske |
| 2004/0106954 | A1* | 6/2004 | Whitehurst ....... A61M 5/14276 607/3 |
| 2006/0074330 | A1* | 4/2006 | Smith .................. A61B 5/0464 600/515 |
| 2006/0136001 | A1 | 6/2006 | Ortega et al. |
| 2006/0241701 | A1 | 10/2006 | Markowitz et al. |
| 2007/0055319 | A1 | 3/2007 | Spadgenske |
| 2007/0173896 | A1 | 7/2007 | Zdeblick |
| 2008/0033490 | A1 | 2/2008 | Giftakis et al. |
| 2008/0086174 | A1 | 4/2008 | Libbus et al. |
| 2008/0086175 | A1 | 4/2008 | Libbus et al. |
| 2008/0208301 | A1 | 8/2008 | Alexander et al. |
| 2008/0221568 | A1 | 9/2008 | Stone |
| 2009/0054949 | A1 | 2/2009 | Alexander et al. |
| 2009/0093857 | A1 | 4/2009 | Markowitz et al. |
| 2010/0057174 | A1 | 3/2010 | Harrison et al. |
| 2010/0069985 | A1* | 3/2010 | Stahmann .......... A61N 1/36185 607/9 |
| 2010/0114200 | A1 | 5/2010 | Krause et al. |
| 2012/0041508 | A1 | 2/2012 | Rousso et al. |
| 2014/0228924 | A1 | 8/2014 | Rousso et al. |

FOREIGN PATENT DOCUMENTS

| | | |
|---|---|---|
| WO | WO 2010/122521 | 1/2010 |
| WO | WO 2010/051482 | 5/2010 |

OTHER PUBLICATIONS

Communciation Pursuant to Article 94(3) EPC dated Sep. 18, 2015 From the European Patent Office Re. Application No. 10717838.6.
International Preliminary Report on Patentability dated Nov. 3, 2011 From the International Bureau of WIPO Re. Application No. PCT/IB2010/051783.
International Search Report and Written Opinion dated Sep. 27, 2010 From the International Search Authority Re. Application No. PCT/IB2010/051783.
Notice of Allowance dated Dec. 6, 2013 From the US Patent and Trademark Office Re. U.S. Appl. No. 13/265,874.
Notice of Allowance dated Dec. 23, 2015 From the US Patent and Trademark Office Re. U.S. Appl. No. 14/254,945.
Official Action dated Jul. 14, 2014 From the US Patent and Trademark Office Re. U.S. Appl. No. 14/254,945.
Official Action dated Jan. 20, 2015 From the US Patent and Trademark Office Re. U.S. Appl. No. 14/254,945.
Official Action dated Jul. 27, 2015 From the US Patent and Trademark Office Re. U.S. Appl. No. 14/254,945.
Georgia State University "Common Wire Gauges", Georgia State University, Physics Department, Web. Jul. 22, 2015.

* cited by examiner

IMPLANTABLE LEAD CONNECTOR

RELATED APPLICATIONS

This application is a continuation of U.S. patent application Ser. No. 14/254,945 filed on Apr. 17, 2014, which is a continuation of U.S. patent application Ser. No. 13/265,874 filed on Oct. 23, 2011, now U.S. Pat. No. 8,706,230, which is a National Phase of PCT Patent Application No. PCT/IB2010/051783 having International Filing Date of Apr. 23, 2010, which claims the benefit of priority of U.S. Provisional Patent Application No. 61/202,958 filed on Apr. 23, 2009. The contents of the above applications are all incorporated by reference as if fully set forth herein in their entirety.

FIELD AND BACKGROUND OF THE INVENTION

The present invention, in some embodiments thereof, relates to active implantable medical devices and, more particularly, but not exclusively, to a device and a method for electrically interconnecting multiple active implantable medical devices Active implantable medical devices are commonly used to sense physiological signals from a target tissue or organ and frequently, in response, to deliver a therapy to the target tissue or organ in the form of electrical stimulation. Some devices are capable of both sensing physiological signals and of delivering therapy in response to predetermined characteristics of the sensed signals. Examples of these include cardiac pacemakers, implantable cardiac defibrillators (ICD), and implantable pulse generators, which deliver electrical stimulation to the heart in response to detection of heart defect symptoms such as arrhythmias, ventricular fibrillation, ventricular tachycardia, and/or congestive heart failure.

Use of active implantable medical devices has increased dramatically in the past few years. These include, in addition to those previously mentioned, devices such as, for example, implantable nerve stimulators, sphincter stimulators, diaphragm stimulators, cochlear implants, implantable drug administration devices, among others. As a result, there is a tendency to see an increasing number of patients require implant of multiple devices to address different therapeutic needs. Generally, each device includes its own leads to sense signals and/or deliver electrical stimulation. Furthermore, each device generally has its own power source which includes batteries requiring periodic replacement.

With the increasing demand for multiple devices, efforts are being made to reduce the number of devices implanted by combining device-related functions. Such is the case, for example, with cardiac defibrillators which many now include pacemaker functions. Additionally, efforts are being made to reduce the number of leads connected to each device and running through the body.

U.S. Pat. No. 5,325,870 "MULTIPLEXED DEFIBRILLATION ELECTRODE APPARATUS" relates to"A defibrillation electrode apparatus which provides defibrillating, pacing, and sensing functions with the use of fewer conductors. Conductor requirements are minimized by solid-state multiplexing that is accomplished at the distal end of the apparatus."

U.S. Pat. No. 5,628,776 "IMPLANTABLE LEAD WITH WARNING SYSTEM" relates to "A cardiac simulation system including a patient warning apparatus. The cardiac stimulator is an implantable pacemaker or defibrillator or combination which can be programmed to automatically alter the voltage of its output stimulus, in particular, to increase the voltage of the output stimulus whenever a condition exists requiring patient notification or warning. A specialized auxiliary lead with a shunt circuit can be connected to a standard socket of a cardiac stimulator header and a standard lead, such as a cardiac pacemaker lead, can then be connected to the auxiliary lead. The auxiliary lead allows a stimulation electrode to be implanted near excitable tissue in a secure fashion to assure stimulation of tissue. The auxiliary lead includes an apparatus for shunting electrical current from the standard stimulation electrode implanted in or near the patient's heart to the auxiliary electrode in the presence of a stimulation pulse with a voltage at or above a preselected level."

SUMMARY OF THE INVENTION

There is provided in accordance with an exemplary embodiment of the invention, an implantable lead connector configured for long term implantation and to electrically interconnect multiple medical devices and to channel electrical signals between said interconnected devices and a target organ, comprising:

a first port adapted to receive a first signal suitable to stimulate a target tissue;

a second port adapted to receive a second signal suitable to stimulate a target tissue; and a third port configured to connect to a target organ, wherein at least one of said first and second ports is configured to connect to a signal generator not integrated with said connector.

In an exemplary embodiment of the invention the connector comprises interconnection circuitry configured to selectively and alternately connect one of said first and second ports to said third port at low impedance and to the other port at high impedance. Optionally said interconnection circuitry is configured to isolate said medical devices from each other. Optionally or alternatively, said interconnection circuitry is configured to allow one of said devices to detect stimulation signals by another of said devices, via said ports.

In an exemplary embodiment of the invention said interconnection circuitry comprises a switch.

In an exemplary embodiment of the invention said interconnection circuitry is powered by and responds to said stimulation signals.

In an exemplary embodiment of the invention said interconnection circuitry comprises voltage-responding impedance circuits.

In an exemplary embodiment of the invention said interconnection circuitry includes a logic circuitry and includes a memory for storing a device state or a time.

In an exemplary embodiment of the invention said interconnection circuitry is configured to generate a blanking having duration on one of said ports in response to a signal on another of said ports.

In an exemplary embodiment of the invention said first and second ports are male connectors and said third port is a female connector. Optionally all of said connectors are standard implantable cardiac connectors.

In an exemplary embodiment of the invention said third port is integrated with a cardiac lead.

In an exemplary embodiment of the invention said connector is integrated with one of said medical devices. Optionally said device is configured to deliver contractility modulation signals in a manner synchronized with an ICD or pacemaker attached to said second port. Optionally or alternatively said device includes sense amplifies resistant to a voltage of at least 2 volts.

In an exemplary embodiment of the invention the third port comprises a connection for a single lead connecting to the target organ. Optionally the single lead is configured to transfer a physiological signal from the target organ to said connector. Optionally or alternatively the single lead is configured to transfer a stimulation signal from said connector to the organ.

In an exemplary embodiment of the invention the stimulation signals are above 2 volts.

There is provided in accordance with an exemplary embodiment of the invention, a method of electrical device interconnection for an implantable connector, comprising:
selecting a first device for electrically stimulating tissue;
selecting a second device for electrically stimulating said tissue; and
coupling said first and said second device to an electrical interconnector. Optionally, said coupling comprises couplings aid first device to an interconnector integral with said second device. Optionally or alternatively the method comprises coupling said interconnector to said tissue. Optionally or alternatively coupling comprises selectively isolating one device from the other device.

In an exemplary embodiment of the invention coupling comprises identifying the operation of one device and raising an impedance to a connection of the second device to said interconnector.

In an exemplary embodiment of the invention coupling comprises selectively blanking one of said devices according to an operation of the other device.

In an exemplary embodiment of the invention coupling comprises providing at least one of said devices with circuitry capable of resisting damage form a signal generated by the other device.

In an exemplary embodiment of the invention coupling comprises conveying physiological signal from said tissue to one of said devices.

In an exemplary embodiment of the invention coupling comprises conveying physiological signal from said tissue to both of said devices.

In an exemplary embodiment of the invention coupling comprises conveying an indication of an operation of one device to the other device via said interconnector.

In an exemplary embodiment of the invention coupling comprises causing one device to act as a slave device to the operation of the other device.

In an exemplary embodiment of the invention coupling comprises programming at least one device with an operational parameter for desired operation with the other device.

In an exemplary embodiment of the invention said first device is a contractility modulator and wherein said second device is a pacemaker or an ICD.

There is provided in accordance with an exemplary embodiment of the invention, a method of using two electrically interconnected medical electrical stimulators, comprising programming at least one of said stimulators with an operational parameter suitable for co-operation with the other stimulator. Optionally said parameter comprises a blanking time. Optionally or alternatively said parameter comprises a delay greater than one second after operation of the other device.

There is provided in accordance with an exemplary embodiment of the invention, an electrical stimulator system, comprising:
a first implantable electrical stimulator;

a second implantable electrical stimulator separate and including separate implantable housing form said first stimulator; and
implantable interconnection circuitry which interconnects said stimulators and a target tissue. Optionally, said circuitry is integrated with said first stimulator. Optionally or alternatively, said first stimulator is a contractility modulator and wherein said second stimulator is an ICD or a pacemaker. Optionally or alternatively said system comprises only a single lead attached to said target tissue. Optionally or alternatively, said interconnection circuitry selectively and alternately isolates one stimulator from the other.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
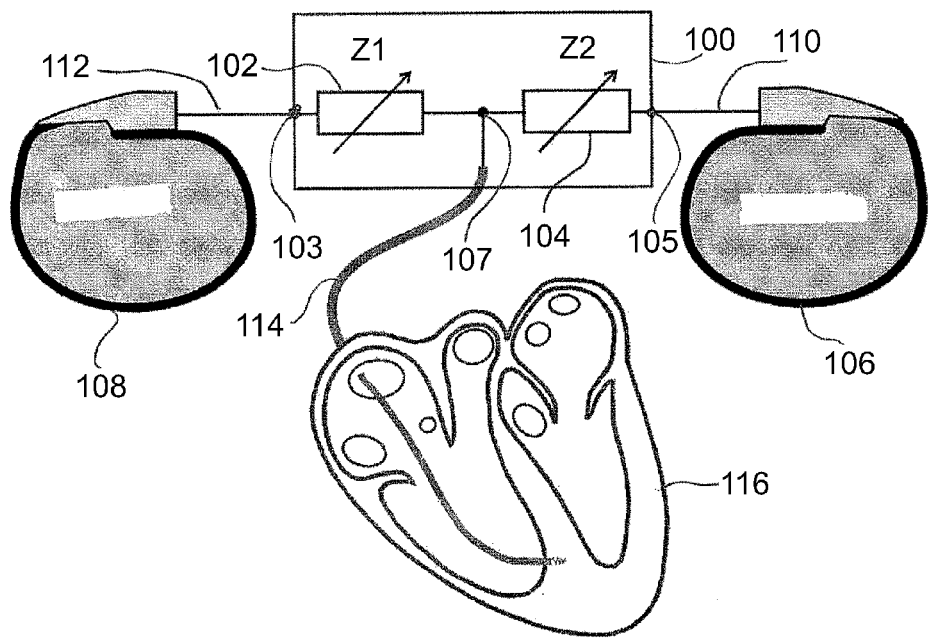
FIG. 1 schematically illustrates an exemplary implantable lead connector with each port including serially connected impedance, according to some embodiments of the present invention.

The present invention, in some embodiments thereof, relates to active implantable medical devices and, more particularly, but not exclusively, to a device and a method for electrically interconnecting multiple active implantable medical devices.

The present invention, in some embodiments thereof, relates to active implantable medical devices and, more particularly, but not exclusively, to a device and a method for electrically interconnecting multiple active implantable medical devices.

An aspect of some embodiments of the present invention relates to an implantable lead connector adapted to connect leads from multiple active implantable medical devices to a single shared (or multiple shared, e.g., 2, 3, 4 or more) implantable lead attachable to a target tissue or organ. Optionally, sensing of a physiological signal in the target tissue or organ is done through the single lead. Optionally, stimulation of the target tissue or organ is done by sending a stimulation signal through the single lead. Additionally or alternatively, use of the connector allows the multiple active implantable devices to share a single lead to sense signals from and/or deliver therapy to the target tissue or organ. Optionally, a number of devices which may be connected through the connector to the single lead are at least 2 devices, at least 3 devices, at least 4 devices or at least 5 devices. In some embodiments, the adapter is not implanted, but, for example, is attached to the skin and/or remains outside the body.

In an exemplary embodiment of the invention the lead connector is used to update a functionality of an implanted device, for example, with added functionality provided by the connector or by an implanted device. Optionally the functionality is an improvement of the implanted device, for example, advanced pacing logic. Optionally or alternatively, the improvement is an additional function, such as ICD for a pacemaker. In an exemplary embodiment of the invention the lead connector protects the devices from each other (e.g., by adding blanking periods) and/or synchronizes the functions of the devices.

While in some embodiments one device is unaware of the other device. Optionally at least one device is programmed to take into account the existence of the other device, for example, by including blanking period when the other device is active. Optionally or alternatively one device reads the operation of the other device, for example, by sensing pacing commands thereof, for purposes such as, for example, timing or inferring of logical state of the heart or other device. Optionally after the operating of one device, the other device delays operation, for example, to allow tissue to recover or based on an estimating of tissue state due to the other device operation (e.g. arrhythmia), for example, for 1 second (or one or 2-5 beats), 5 seconds, 10 seconds, a minute, 5 minutes, one hour, a day or greater or intermediate durations.

In an exemplary embodiment of the invention only a single lead is attached to the heart. Optionally, however, additional leads, which optionally bypass the connector, are used. Optionally the connector is used to provide blanking or current protection also for unshared leads. In one example, different devices have different sensor leads (e.g., blood pressure sensor and flow sensor). In another example, sensor leads are also shared.

In an exemplary embodiment of the invention the connector comprises a lead optionally integrated with a small capsule, which small capsule is configured to attach to an ICD and a different medical device. Optionally the lead has a screw type electrode (or other tissue attaching electrode) and sensing electrode at its tip, suitable for ICD. Optionally the capsule includes a cable suitable for connecting to an ICD and a cable suitable to connect to a CCM or other device. Optionally the capsule has a volume of less than 20 cubic cm, 10 cubic cm, 5 cubic cm or 2 cubic centimeters Optionally the capsule is thinner than 5 mm, 3 mm, 2 mm. Optionally the CCM (or other device) acts as a slave device which modulates, modifies, adds signals and/or modifies its behavior according to the ICD behavior. Optionally the CCM (or other device) has sense amplifiers configured to resist damage when hit with a defibrillation and/or pacing voltage.

Optionally the connector includes circuitry, for example, powered by pacing pulses or by an internal battery, which applies a logic, such as blanking to ports thereof.

In another embodiment, a CCM device is configured to include an input to receive an ICD lead. Optionally the connector logic as described herein is included in the CCM or other device. Optionally the CCM is provided with leads suitable for both CCM and ICD. Optionally the lead includes one or two defibrillation electrodes and two electrodes (e.g., ring and screw-in) used for pacing and for supplying a CCM signal. Alternatively, at least one extra CCM lead is provided.

Connection of a single lead to two or more active implantable devices where at least one of them is capable of stimulating a target tissue or organ generally cannot be done with a passive signal splitter. One reason is that the stimulation signal delivered by one of the devices may cause inappropriate functioning or even damage to sensing or other circuitry in the other devices. In some cases, the impedance of the other devices may be altered which may cause impedance mismatching between the devices. Furthermore, the stimulation signal delivered by the device may be shunted by the protection circuitry of the other devices instead of being delivered to the target tissue or organ, or otherwise be provided to target tissue with wrong parameters.

However, in some embodiments of the invention, a passive splitter is used, or, in some cases, only one port is protected. Optionally a device connected to an unprotected port is designed to include sense amplifiers and/or other circuitry resistant to stimulation voltage, for example, 1 volt, 2 volts, 4 volts, 7 volts, 10 volts, 50 volts or intermediate or larger voltages, for example, as may be provided by pacing, contractility modulation and/or defibrillation.

In some exemplary embodiments, the active implantable medical devices may include cardiac pacemakers, defibrillators, pacing defibrillator (DDD-IDC, dual chamber; ICD-VVI, single pacing), implantable pulse generators (IPG) for CCM (Cardiac Contractility Modulation), and devices for cardiac resynchronization such as DDD-CRT, CRT-D, and CRT. Optionally, the active medical devices include IPG for blood pressure control, implantable nerve stimulators, sphincter stimulators, diaphragm stimulators, cochlear implants, and implantable drug administration devices.

In some exemplary embodiments, the implantable lead connector is further adapted to connect leads from one or more external active medical devices to the single implantable lead leading to the target tissue or organ. Optionally, the leads from the external active medical devices are inserted into a patient's body through an appropriate transcutaneous port. Optionally, the connector is adapted to connect leads from one or more external active medical devices and from one or more active implantable medical devices to the single implantable lead leading to the target tissue or organ. Additionally or alternatively, the external active medical devices include medical devices adapted to perform similar functions as those performed by the implantable active medical devices and are located externally to a patient's body. Optionally, the external active medical devices are temporarily attached to the connector.

In some exemplary embodiments, an existing implanted device may be connected to the connector with a new devices being implanted for sharing a single lead. For example, an implanted pacemaker may be connected to the connector together with a new IPG. Optionally, two implanted devices may be connected to the connector for sharing a single lead.

In some exemplary embodiments, the connector includes multiple device ports to which the leads from the multiple devices are connected. Optionally, a portion of the device ports each include a variable impedance element for varying an impedance of the port. Optionally, varying an impedance of the device port allows for control of a current flow to and/or from the device attached to the port. Optionally, the connector acts as a "switch" switching signal flow between attached devices through the multiple device ports to and from the target tissue or organ. Optionally, a high impedance device port limits flow of the stimulation signal from the connector to the attached device, essentially switching "off" the device. Optionally, the high impedance is greater than or equal to 50 kOhms, for example, 60 kOhms, 80 kOhms, 100 kOhms, 150 kOhms, 200 kOhms or more. Optionally, a low impedance port allows signal flow through the port to and from the device, essentially switching "on" the device. Additionally or alternatively, a low impedance device port allows flow of the stimulation signal generated by an attached device through the connector to the target tissue or organ. Additionally or alternatively, the low impedance device port allows flow of the physiological signal from the target tissue or organ through the connector to the attached medical device. Optionally, the serial impedance during sensing (physiological signal) is less than or equal to 100 kOhms, for example, 80 kOhms, 60 kOhms, 40 kOhms, 20 kOhms, less than 20 kOhms. Optionally, the shunt impedance is lower than 50 Ohms, for example, 40 Ohms, 30 Ohms, 20 Ohms, 10 Ohms or less.

In some exemplary embodiments, the connector includes a target port to which the single implantable lead is attached. Optionally, the multiple device ports are parallely connected to one another and serially to the target port (for example, schematically in a Y-type or T-type circuit configuration). Optionally, the variable impedance element in the device port is serially connected between the attached device and the target port (to the single lead leading to the target tissue or organ).

In some exemplary embodiments, the variable impedance elements in the device ports are current dependent. Optionally, a current limiting circuit wherein the impedances of the ports vary as a function of the current flowing through the circuit is used. Such a current limiting circuit may be implemented using transistors, for example field effect transistors, between two or more device ports together. An increase in current on one side of the circuit will cut off the other side of the circuit, so that stimulation signal flowing in through one device port will cut off the other device port. Optionally, the target port is connected to the circuit so that the stimulation signal flows through the single lead to the target tissue or organ.

In some embodiments, the variable impedance elements in the device ports are voltage dependent. Optionally, the impedance of a first device port is dependent on a voltage drop across the variable impedance element in a parallely connected second device port. Optionally, a low voltage drop across the impedance element results in a low impedance at the first device port (low impedance port). Additionally or alternatively, a relatively high voltage drop across the impedance element, for example due to a relatively high current of the stimulation signal, causes an increase in the impedance of the first device port (high impedance port). Optionally, the variable impedance element includes a voltage-dependent impedance element connected in parallel between each device and the lead.

In some exemplary embodiments, a front-end circuitry of a device connected to a high impedance port is protected from the stimulation current. Optionally, a sensing channel in the device is substantially blanked by the high impedance, allowing a relatively fast recovery from stimulation current artifacts. Additionally or alternatively, the increase in impedance in the port substantially prevents the stimulation signal from being shunted by a protection circuitry in the device. As noted herein, in some embodiments blanking is provided by the device and in others by the connector.

In some exemplary embodiments, the connector connects a first device to a high impedance port, switching off the port, when a second device generates the stimulation signal (the second device is connected to a low impedance port). Optionally, the stimulation signal is routed through the connector to the single lead, bypassing the high impedance port. Optionally, the stimulation signal is generated responsive to a physiological signal. Optionally, the device ports are switched on at low impedance while the physiological signal from the target tissue or organ is being sensed through the single lead. Additionally or alternatively, the physiological signal is routed through the single lead and through the connector to each device. Optionally, the connector is configured to route the physiological signal to either the first or second device by adjusting the impedances at anyone of, or both, ports. Optionally, the connector is configured to route the stimulation signal from either the first or second device by adjusting the impedances at anyone of, or both, ports.

In some exemplary embodiments, the connector is configured to connect multiple active implantable devices to a plurality of single leads for sensing and/or stimulating different target tissues in a same organ. For example, in the heart, a first single lead may be attached to the septum, a second single lead may be attached to the right atrium, and a third single lead may be attached to the right ventricular. Optionally, the plurality of single leads is used for sensing and/or stimulating different target organs (or tissues in different organs). For example, one single lead may be attached to the brain while a single lead may be attached to the spinal cord. Optionally, two or more connectors may be connected together for increasing a number of single leads which can be attached to different tissues and/or organs. Optionally, a greater number of devices can be attached. Optionally, the connectors are connected in series and/or in parallel. Additionally or alternatively, a serial connection of the connectors may allow override of one connector over the decision of the other. Optionally, for unidirectional current flow, a parallel flow of the connectors will allow current flow in a specific direction based on the control of each connector. Optionally, one of the isolation circuits which isolate one device from the other device may include a diode or other circuit which prevents backflow.

In some exemplary embodiments, stimulation signals are sequentially generated by each device, the impedances at the ports varied accordingly in the connector (low impedance at the port connected to device generating the stimulation signal and high impedance at the port connected to the second device, and alternating respectively as each device generates a stimulation signal). Optionally, a plurality of stimulation signals is generated by a same device. Optionally, the port impedances are varied according to any order in which the devices generate the stimulation signal. Appropriate circuitry may be included in the connector for synchronizing with the devices. Optionally, the circuitry can emulate a logic of one or both devices enabling the connector (or other device) to anticipate the generated stimulation signal and/or to determine when to apply blanking on sensing and/or stimulation.

In some embodiments, the connector includes a controller and associated circuitry for varying the impedances at the ports. Optionally, the controller varies the impedance in one or more ports according to parameters associated with the device connected to the port. For example, the impedance of the port may be adjusted according to the type of medical device connected, model of the device, a manufacturer of the device, a power rating of the device, a stimulation current of the device, and an input impedance of the device, among others. Optionally, the controller varies the impedance in one or more ports according to an activation state of the devices; pacing, sensing, stimulating, and the like. Optionally, adjusting the impedance in a port according to the connected device enhances blanking. Additionally or alternatively, the controller generates signals simulating the physiological signal to cause the devices to generate a stimulation signal, for example to force a defibrillation. Additionally or alternatively, information as to the parameters associated with the connected device is received through the device leads connected to the ports. Optionally, a dedicated data line is used to input the information to the controller. Optionally, the dedicated data line to the connector can serve as a "reader" which talks to the connected devices. Optionally, the information is input into the controller when the device is initially connected by a physician. Additionally or alternatively, the information is preprogrammed into the controller. Optionally, the information is input by the physician through a wireless connection. Optionally, the controller enables the connector to be used by the connected devices as an add-on logic module for adding to, substituting and or replacing functions in the devices. Additionally or alternatively, the connector can block switch off one device and listen to the second device, switching on the first device when required. Optionally, the connector can listen to the single lead and switch on the first device when required. Optionally, the connector can allow the first device to listen to the second device.

In some exemplary embodiments, the connector includes passive electronic components such as, for example, resistors, capacitors, and coils. Optionally, the connector includes semiconductor devices such as, for example, transistors and diodes.

In some exemplary embodiments, the connector allows for power to be shared between attached medical devices. Optionally, a connected device is powered by another connected device. Optionally, a connected device is powered by the connector. Optionally, powering multiple connected devices from a single device (or the connector) substantially allows for decreasing a size of the connected devices. Optionally, powering from a single device substantially eliminates a need for periodic replacement of a battery in the other devices (only one device or the connector needs to have batteries changed).

In some exemplary embodiments, the connector includes a power supply for powering included electronics. Optionally, the power supply supplies power to the connected medical devices. Optionally, the power supply includes a battery. Optionally, power is supplied from one or more of the attached implantable medical devices. Optionally, a power harvester circuit (e.g., harvesting from the body, from an external power transmitter and/or the stimulation signals) is included for charging the battery and/or a power-storage element. In an exemplary embodiment of the invention the start of a stimulation signal provides sufficient power to activate any electronics which further determine the logic of the connector. Optionally the two input ports are normally at a high impedance at least part of the time and when power is detected at one port, that power is used for logic which lowers the impedance at that port. Optionally if power is detected at both ports, one port is defined as a master or possibly the logic is set so no port is opened.

In some exemplary embodiments, the connector includes a housing made from a biocompatible material such as, for example, a silicon rubber casing. Optionally, the housing includes a disk shape. Optionally, the connector is partly flexible. Additionally or alternatively, the connector can be molded to a shape of one of the devices for physically fitting the connector against the device. Optionally, the connector is preshaped to fit against the device. Optionally, the connector is rigidly shaped. Optionally, the silicon encases the included electronics and connector blocks. Additionally or alternatively, the electronics is hermetically sealed in metallic or ceramic materials. Optionally, the electronics is coated with polymeric, glass, or ceramic layers for protection from environmental stresses such as, for example, mechanical stresses, exposure to liquids and the like.

In some exemplary embodiments, the connector includes a greater number of ports than are shared between connected devices. Optionally, several of the ports are configured for passing leads through the connector, for example, from the device through the connector to a target tissue or organ. These ports do not include varying impedances.

In some exemplary embodiments, the connector is included in one of the implantable medical devices. Optionally, the connector shares the resources of the medical device, such as, for example the device's controller, memory, and other circuitry. Optionally, the connector can be removably attached to the device and share the resources of the device. Optionally, the connector shares its resources with the device. Additionally or alternatively, the connector can serve as an interface to physically attach two devices. Optionally, the connector shares the resources of one or both of the devices.

Following is described an exemplary application of an IPG and an ICD connected to a connector so as to enable the devices to share leads and reduce a number of leads attached to a target tissue or organ, according to some exemplary embodiments.

The connector interconnects an IPG for CCM therapy such as, for example, the OPTIMIZER III IPG developed by Impulse Dynamics Ltd, Israel with dual-chamber pacing ICD (DDD-ICD). Optionally, the IPG is connected to a single-chamber pacing ICD (ICD-VVI). In a typical configuration without use of the connector, 5 leads are delivered intravenously to the heart. These include:

a) ICD's Right-Atrial lead;
b) ICD's Right-Ventricular lead (which includes a defibrillation shock electrode);
c) OPTIMIZER III's Right-Atrial (RA) lead;
d) OPTIMIZER III's Right-Ventricular (RV) lead; and
e) OPTIMIZER III's Right-Ventricular-Septum (LS) lead.

In some exemplary embodiments, leads are shared between the IPG and the ICD through the connector, reducing a number of cardiac leads delivered intravenously into the heart. Optionally, a current carrying capacity of the leads is up to 50 mA or more, for example, up to 10 mA, up to 20 mA, up to 30 mA, up to 40 mA or intermediate values. Optionally, a number of leads is determined by the impedance of the leads. Optionally, common leads from the IPG and the ICD connect to the connector, and from there a single cardiac lead goes to the heart. Optionally, the leads connecting the devices to the connector include Bipolar IS-1 to IS-1 cables. Optionally, the leads connecting the devices to the connector are bundled.

In some embodiments, two leads are shared between the IPG and the ICD through the connector; the right atrial lead and the right ventricular lead. Optionally, these leads are connected through the connector to the heart. Optionally, the right ventricular septum lead is connected directly from the IPG to the heart. Additionally or alternatively, only three leads are inserted in the heart (as compared to five leads without the connector). Optionally, one lead is shared and three leads enter the heart. Additionally or alternatively, the IPG is activated by a single lead. Optionally, a left ventricle lead suitable for CCM signal and pacing is shared with an ICD through the connector. Optionally, the left ventricle lead is epicardial. Optionally, the IPG includes the connector (built-in) and connects to the ICD by means of a DF-4 standard tetrapolar in-line connector. Optionally, the controller in the IPG controls the varying of the port impedances in the connector.

In some exemplary embodiments, the IPG actively blanks the ICD sensing for the period of CCM delivery. Optionally, ICD sensing parameters require minimum, if any, setting. Optionally, the IPG uses the information related to pacing of the RA and/or RV to change mode to different set of CCM parameters. Additionally or alternatively, the IPG uses the information to change different windows setting. Optionally, the IPG uses information related to shock delivery such as, for example, using a sensing coil mounted on the lead, if a clear artifact is sensed on the other leads, to inhibit CCM or other treatment for a certain time period. Optionally such sensing is used instead of or in addition to a connector.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring now to the drawings, FIG. 1 schematically illustrates an exemplary implantable lead connector 100 including a variable impedance element 102 in device port 103, and a variable impedance element 104 in device port 105, according to some embodiments of the present invention. Optionally, connector 100 is adapted to vary an impedance of impedance element 102 and/or impedance element 104 for routing a current flow through the connector between active implantable medical devices 108 and/or 106 and a target organ 116. Optionally, connector 100 corroborates that current flow is according to planned parameters. Optionally, connector 100 corroborates lead quality for sensing by impedance measurements of the lead. Optionally, the impedance of impedance element 102 and/or impedance element 104 varies as a function of the current flowing through the impedance elements. Optionally, impedance elements 102 and 104 include a current limiting circuit.

In some exemplary embodiments, connector 100 includes three ports, device port 103 and device port 105 to each of which a medical device is connected, and target port 107 to which single lead 114 is connected. Optionally, device port 103, device port 105, and target port 107 are connected in a T-type circuit configuration with the device ports parallel to one another. Optionally, connected to device port 103 through a cable 112 is medical device 108. Optionally, connected to device port 105 through a cable 110 is medical device 106. Optionally, medical devices 106 and 108 are a same active implantable medical device. Optionally, medical devices 106 and 108 are different types of active implantable medical devices. Connected to target port 107 through lead 114 is target organ 116. Optionally, target organ 116 is a heart.

In some exemplary embodiments, variable impedance element 102 in device port 103 is serially connected through lead 112 to medical device 108 on one side, and on the other side through lead 114 to target organ 116. Optionally, variable impedance element 104 in device port 105 is serially connected through lead 110 to medical device 106 on one side, and on the other side through lead 114 to target organ 116.

In some exemplary embodiments, lead 114 is adapted to sense a physiological signal in target organ 116 and to transfer the signal to connector 100. Optionally, lead 114 includes a single lead. Optionally, lead 114 is adapted to transfer a stimulation signal from connector 100 to target organ 116. Optionally, lead 114 includes a plurality of leads, for example, two single leads attached to different tissues which are to receive a similar stimulation signal. Optionally, connector 100 is configured to switch between the two single leads for sensing and stimulating two different tissues at different times. Optionally, connector 100 is configured to stimulate the two different tissues at the same time.

In some exemplary embodiments, a mode of operation of connector 100 is as follows:

Lead 114 senses a physiological signal in target organ 116 and transfers the signal to connector 100. The signal flows across impedances 102 and 104 to medical devices 108 and 106, respectively. Optionally, impedances 102 and 104 include low impedances. Devices 108 and 106 each receive the signal and optionally based on an analysis of the signal according to predetermined criteria, one of the devices will generate a stimulation signal. Assuming for exemplary purposes that device 108 generates the stimulation signal, impedance 102 remains low while impedance 104 goes high. Optionally, the impedance of impedance 102 may increase somewhat but remains sufficiently low so as to not interfere with the stimulation signal. The stimulation signal then flows from device 106 through lead 114 to target organ 116. Flow of stimulation signal through impedance 104 to medical device 106 is substantially prevented by the high impedance. Optionally, front-end circuitry in medical device 106 is protected from possible damage by the stimulation signal. Optionally, possible shunting of the stimulation signal by medical device 106 is prevented, allowing the stimulation signal to reach target organ 116 through lead 114.

Figure 2:
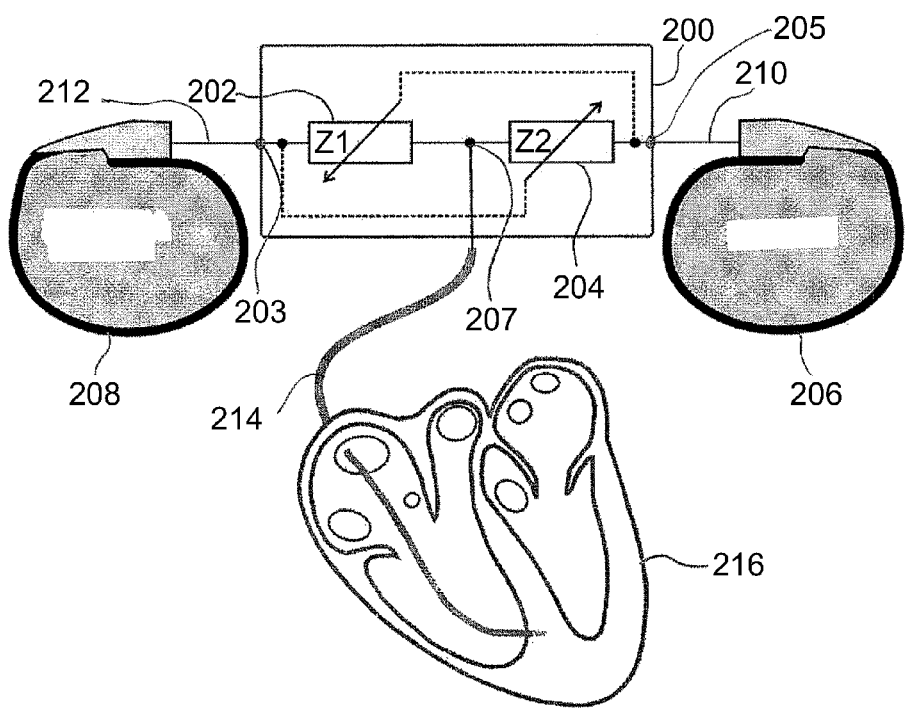
FIG. 2 schematically illustrates an exemplary lead connector with each port including a voltage-dependent serially connected impedance, according to some embodiments of the present invention.

Reference is now made to FIG. 2 which schematically illustrates an exemplary implantable lead connector 200 including a variable impedance element 202 in device port 203, and a variable impedance element 204 in device port 205, according to some embodiments of the present invention. In an exemplary embodiment of the invention, connector 200 is adapted to vary an impedance of impedance 202 and/or impedance 204 for routing a current flow through the connector between active implantable medical devices 208 and/or 206 and a target organ 216. Optionally, connector 200 corroborates that current flow is according to planned parameters. Optionally, connector 200 corroborates lead quality for sensing by impedance measurements of the lead. Optionally, medical devices 208 and 206, and target organ 216, are similar to that shown in FIG. 1 at 108, 106, and 116, respectively. Optionally, impedance element 202 and impedance element 204 include voltage-dependent impedances.

In some exemplary embodiments, connector 200 includes three ports, device port 203 and device port 205 to each of which a medical device is connected, and target port 207 to which single lead 214 is connected. Optionally, device port 203, device port 205, and target port 207 are connected in a T-type circuit configuration with the device ports parallel to one another. Optionally, connected to device port 203 through a cable 212 is medical device 208. Optionally, connected to device port 205 through a cable 210 is medical device 206. Connected to target port 207 through lead 214 is target organ 216.

In some exemplary embodiments, variable impedance element 202 in device port 203 is serially connected through lead 212 to medical device 208 on one side, and on the other side through lead 214 to target organ 216. Optionally, variable impedance element 204 in device port 205 is serially connected through lead 210 to medical device 206 on one side, and on the other side through lead 214 to target organ 216. Optionally, cable 212, cable 210, and lead 214 is similar to that shown in FIG. 1 at 112, 110, and 114, respectively.

In some exemplary embodiments, the impedance of impedance element 202 goes high when a voltage drop across impedance element 204 due to a stimulation signal increases, while the impedance of impedance element 204 is low. Optionally, the impedance of impedance element 204 goes high when a voltage drop across impedance element 202 due to the stimulation signal increases, while the impedance of impedance 202 is low.

In some exemplary embodiments, a mode of operation of connector 200 is similar to that of connector 100 with a difference, as previously mentioned, that one impedance goes high when the voltage drop increases across the second impedance due to the stimulation signal; the second impedance remaining low (may increase somewhat but remains sufficiently low so as to not interfere with the stimulation signal).

Figure 3:
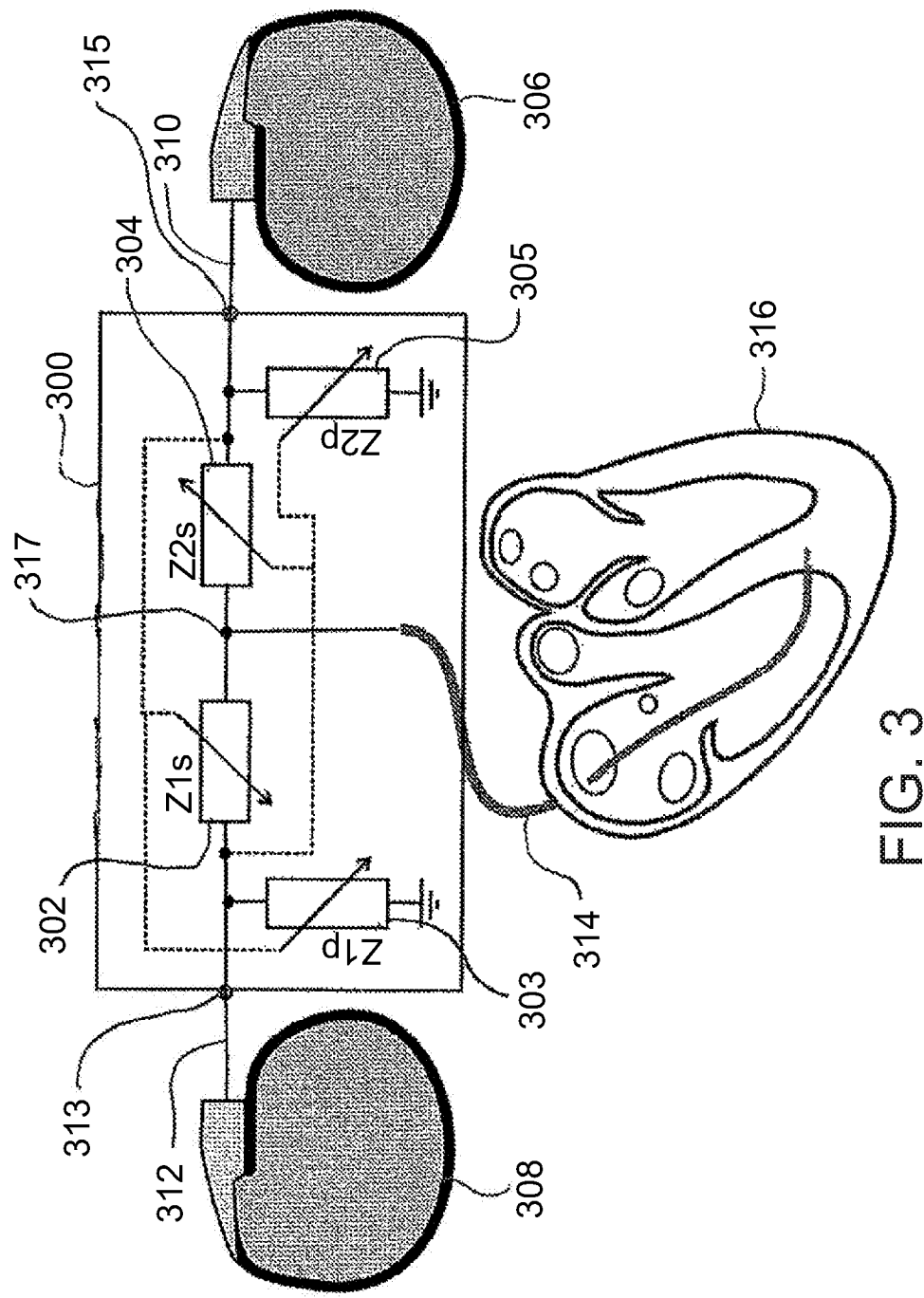
FIG. 3 schematically illustrates an exemplary lead connector with each port including a voltage-dependent serially connected impedance and a voltage-dependent parallel connected impedance, according to some embodiments of the present invention.

Reference is now made to FIG. 3 which schematically illustrates an exemplary implantable lead connector 300 including a voltage-dependent serially connected impedance element 302 and a voltage-dependent parallel connected impedance element 303 in device port 313, and a voltage-dependent serially connected impedance element 304 and a voltage-dependent parallel connected impedance element 305 in device port 315, according to some embodiments of the present invention. Increasing the impedance of an already high impedance port serves to provide added protection to front end circuitry in the device from the stimulation current. Additionally, blanking of the sensing channel is substantially enhanced by the high impedance, allowing very fast recovery from stimulation current artifacts. Furthermore, the increase in impedance in the port substantially prevents the stimulation signal from being shunted by the protection circuitry in the device.

In some exemplary embodiments, connector 300 is adapted to vary an impedance of impedance elements 302 and 303, and/or impedance elements 304 and 305, for routing a current flow through the connector between active implantable medical devices 308 and/or 306 and a target organ 316. Optionally, connector 300 corroborates that current flow is according to planned parameters. Optionally, connector 300 corroborates lead quality for sensing by impedance measurements of the lead. Optionally, medical devices 308 and 306, and target organ 316, are similar to that shown in FIG. 2 at 208, 206, and 216, respectively.

In some exemplary embodiments, connector 300 includes three ports, device port 313 and device port 315 to each of which a medical device is connected, and target port 317 to which single lead 314 is connected. Optionally, device port 313, device port 315, and target port 317 are connected in a T-type circuit configuration with the device ports parallel to one another. Optionally, connected to device port 313 through a cable 312 is medical device 308. Optionally, connected to device port 315 through a cable 310 is medical device 306. Connected to target port 317 through lead 314 is target organ 316.

In some exemplary embodiments, the impedances of impedance elements 302 and 303 go high when a voltage drop across impedance elements 304 and 305 due to stimulation signal increases, while the impedance of impedance elements 304 is low and 305 is high. Optionally, the impedance of impedance elements 304 and 305 go high when a voltage drop across impedance elements 302 and 303 due to the stimulation signal increases, while the impedance of impedance elements 302 is low and 303 is high. A low series impedance element and a high parallel impedance element in the port connected to the medical device generating the stimulation signal maintains the port switched "on". A high series impedance element and a high parallel impedance element in the port maintains the port switched "off". A low parallel impedance element substantially shunts the port.

In some exemplary embodiments, a mode of operation of connector 300 is similar to that of connector 200 with a difference that the parallel impedances provide each medical device with additional protection from the stimulation signal generated by the other device. Optionally, a recovery of sensing function in the protected medical devices is enhanced.

Figure 4:
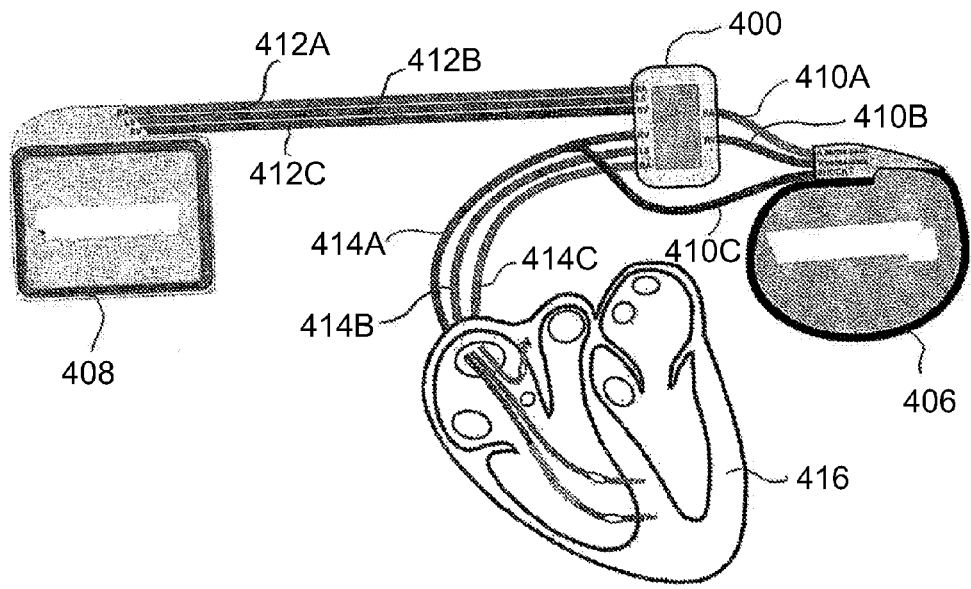
FIG. 4 schematically illustrates an exemplary configuration for interconnecting an IPG with a DDD-ICD using an implantable lead connector, according to some embodiments of the present invention.

Reference is now made to FIG. 4 which schematically illustrates an exemplary configuration for interconnecting an IPG 408 with a DDD-ICD 406 using an implantable lead connector 400, according to some embodiments of the present invention.

Optionally, lead connector 400, IPG 408 and DDD-ICD 406 are similar to that shown in FIG. 1 at 100, 108 and 106. Alternatively, lead connector 400, IPG 408 and DDD-ICD 406 are similar to that shown in FIG. 2 at 200, 208 and 206. Alternatively, lead connector 400, IPG 408 and DDD-ICD 406 are similar to that shown in FIG. 3 at 300, 308 and 306. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

In some exemplary embodiments, 2 leads are shared between IPG 408 and ICD 406 through connector 400, reducing a number of cardiac leads delivered intravenously into the heart from 5 leads to 3 leads. Entering connector 400 from DDD-ICD 406 are 2 cables, a right atrial (RA) cable 410A and a right ventricular (RV) cable 410B. Entering connector 400 from IPG 408 for sharing are two cable, RA cable 412A and RV cable 412C. Optionally, a right ventricular septum lead (LS) 412B is routed through connector 400 to a different port (without sharing). Leading from connector 400 to a heart 416 are 3 cables, an RV cardiac lead 414A to which is connected a shock electrode 410C from ICD 406, an RA cardiac lead 414C, and LS cardiac lead 414B.

Figure 5:
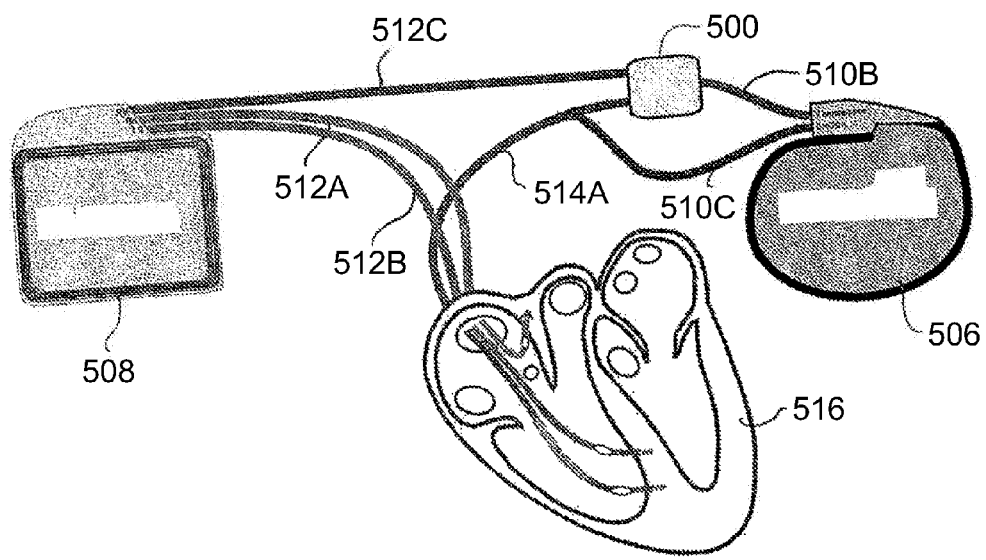
FIG. 5 schematically illustrates an exemplary configuration for interconnecting an IPG with a DDD-ICD using an implantable lead connector, according to some embodiments of the present invention.

Reference is now made to FIG. 5 which schematically illustrates an exemplary configuration for interconnecting an IPG 508 with a ICD-VVI 506 using an implantable lead connector 500, according to some embodiments of the present invention. Optionally, lead connector 500, IPG 508 and DDD-ICD 506 are similar to that shown in FIG. 1 at 100, 108 and 106. Optionally, lead connector 500, IPG 508 and DDD-ICD 506 are similar to that shown in FIG. 2 at 200, 208 and 206. Optionally, lead connector 500, IPG 508 and DDD-ICD 506 are similar to that shown in FIG. 3 at 300, 308 and 306. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

In some exemplary embodiments, 1 lead is shared between IPG 508 and ICD 506 through connector 500, reducing a number of cardiac leads delivered intravenously into the heart from 4 leads to 3 leads. Entering connector 500 from ICD 506 is 1 cable, a right ventricular (RV) cable 510B. Entering connector 500 from IPG 508 for sharing is one cable, RV cable 512C. Leading from connector 500 to a heart 516 is 1 cable, an RV cardiac lead 514A to which is connected a shock electrode 510C from ICD 506. Optionally, leading directly from IPG 508 to heart 516 are 2 cables, an RA cardiac lead 512A, and an LS cardiac lead 512B.

Figure 6:
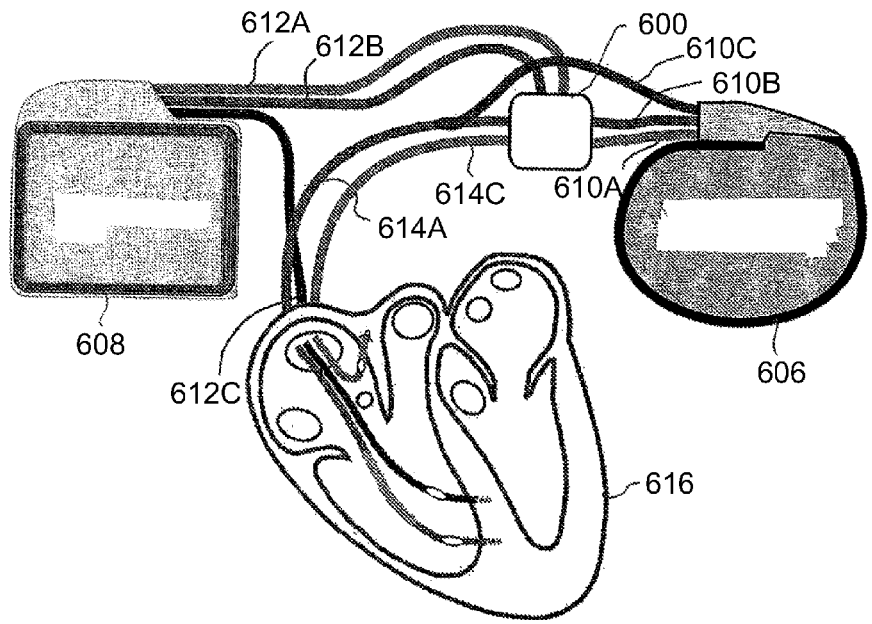
FIG. 6 schematically illustrates an exemplary configuration for interconnecting an IPG with a DDD-ICD using an implantable lead connector, according to some embodiments of the present invention.

Reference is now made to FIG. 6 which schematically illustrates an exemplary configuration for interconnecting an IPG 608 with a DDD-ICD 606 using an implantable lead connector 600, according to some embodiments of the present invention. Optionally, lead connector 600, IPG 608 and DDD-ICD 606 are similar to that shown in FIG. 1 at 100, 108 and 106. Optionally, lead connector 600, IPG 608 and DDD-ICD 606 are similar to that shown in FIG. 2 at 200, 208 and 206. Optionally, lead connector 600, IPG 608 and DDD-ICD 606 are similar to that shown in FIG. 3 at 300, 308 and 306. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

In some exemplary embodiments, 2 leads are shared between IPG 608 and ICD 606 through connector 600, reducing a number of cardiac leads delivered intravenously into the heart from 5 leads to 3 leads. Entering connector 600 from DDD-ICD 606 are 2 cables, a right atrial (RA) cable 610A and a right ventricular (RV) cable 610B. Entering connector 600 from IPG 608 for sharing are two cable, RA cable 612A and RV cable 612B. Leading from connector 600 to a heart 616 are 2 cables, an RV cardiac lead 614A to which is connected a shock electrode 610C from ICD 606 and an RA cardiac lead 614C. Optionally, leading directly from IPG 608 to heart 616 is 1 cable, an LS cardiac lead 612C.

Figure 7:
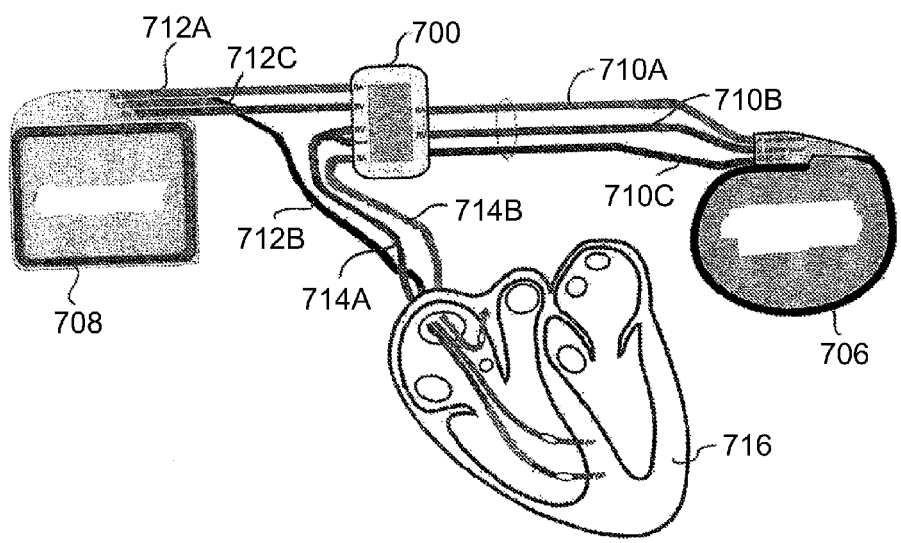
FIG. 7 schematically illustrates an exemplary configuration for interconnecting an IPG with a ICD-VVI using an implantable lead connector, according to some embodiments of the present invention.

Reference is now made to FIG. 7 which schematically illustrates an exemplary configuration for interconnecting an IPG 708 with an ICD-VVI 706 using an implantable lead connector 700, according to some embodiments of the present invention. Optionally, lead connector 700, IPG 708 and ICD 706 are similar to that shown in FIG. 1 at 100, 108 and 106. Optionally, lead connector 700, IPG 708 and ICD 706 are similar to that shown in FIG. 2 at 200, 208 and 206. Optionally, lead connector 700, IPG 708 and ICD 706 are similar to that shown in FIG. 3 at 300, 308 and 306. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

In some exemplary embodiments, 2 leads are shared between IPG 708 and ICD 706 through connector 700, reducing a number of cardiac leads delivered intravenously into the heart from 5 leads to 3 leads. Entering connector 700 from ICD 706 are 2 cables, a right atrial (RA) cable 710A and a right ventricular (RV) cable 710B. Entering connector 700 from IPG 708 for sharing are two cable, RA cable 712A and RV cable 712C. Optionally, a shock electrode 710C ICD 706 is routed through connector 700 to a different port (without sharing). Leading from connector 700 to a heart 716 are 2 cables, an RV cardiac lead 714A to which is connected shock electrode rerouted 710C, and an RA cardiac lead 714C. Optionally, leading directly from IPG 708 to heart 716 is 1 cable, an LS cardiac lead 712B.

Figure 8:
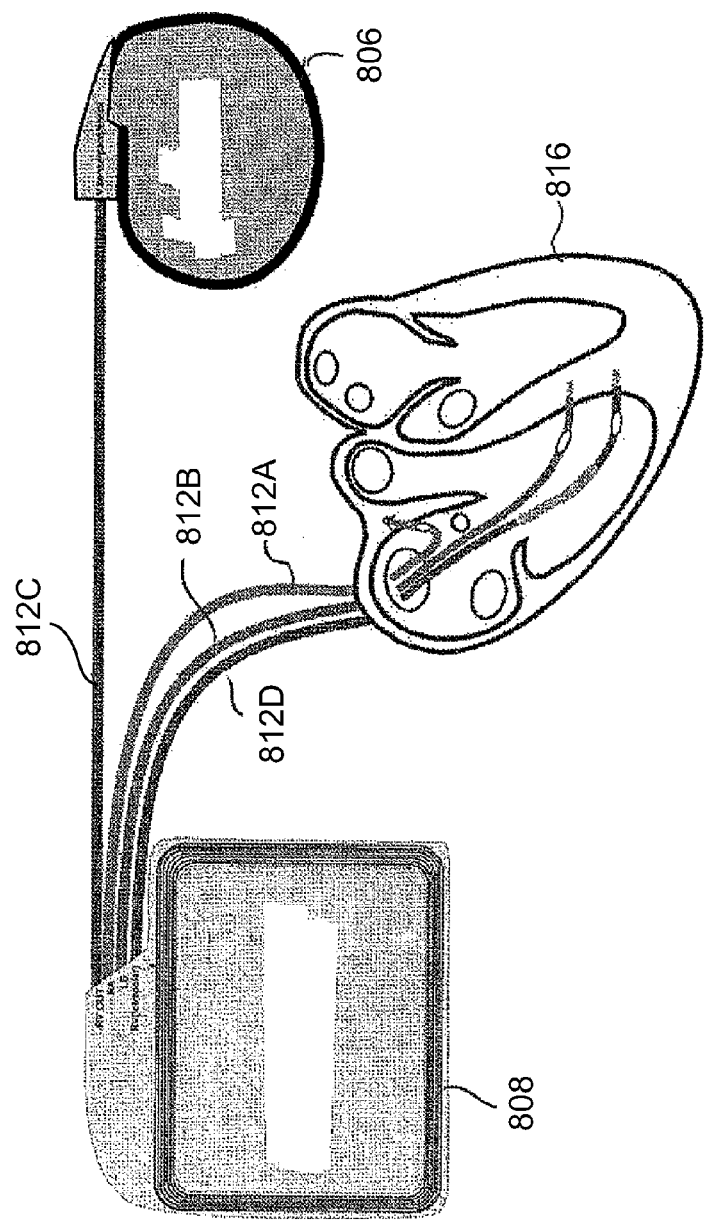
FIG. 8 schematically illustrates an exemplary configuration for interconnecting an IPG with a ICD-VVI using an implantable lead connector, according to some embodiments of the present invention.

Reference is now made to FIG. 8 which schematically illustrates an exemplary configuration for interconnecting an IPG 808 with an ICD-VVI 806 using an implantable lead connector included in the IPG, according to some embodiments of the present invention. Optionally, the lead connector, IPG 808 and ICD 806 are similar to that shown in FIG. 1 at 100, 108 and 106. Optionally, the lead connector, IPG 808 and ICD 806 are similar to that shown in FIG. 2 at 200, 208 and 206. Optionally, the lead connector, IPG 808 and ICD 806 are similar to that shown in FIG. 3 at 300, 308 and 306. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

In some exemplary embodiments, ICD 806 is connected to the connector in IPG 808 through a DF-4 standard tetrapolar in-line connector cable 812C. Optionally, cable 812C includes in a single cable the RV cable and the shock electrode from ICD 806.

This type of connection allows for a number of cardiac leads delivered intravenously into the heart to be reduced to 3. Leading from the connector in IPG 808 to the heart are RA cable 812A, LS cable 812B, and RV cable 812D.

Figure 9:
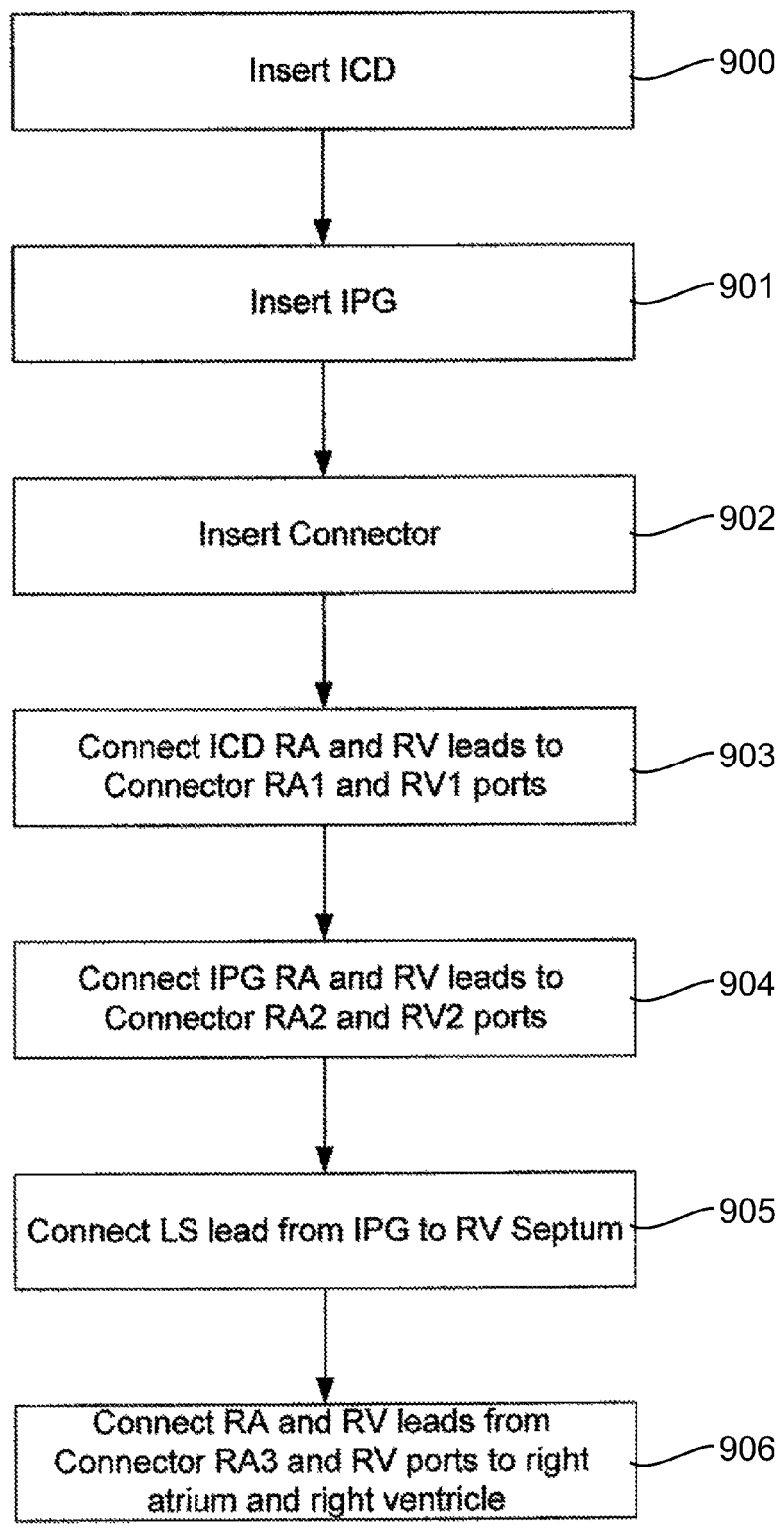
FIG. 9 illustrates a flow chart of a method of interconnecting an IPG with a DDD-ICD using an implantable lead connector, according to some embodiments of the present invention.

Reference is now made to FIG. 9 which illustrates a flow chart of an exemplary method of interconnecting an IPG with a DDD-ICD using an implantable lead connector, according to some embodiments of the present invention.

The exemplary method is described below with reference to the exemplary configuration previously described and shown in FIG. 6 for interconnecting multiple active implantable medical devices. It should be evident to a person skilled in the art that numerous other configurations for interconnecting a plurality of active implantable medical devices are possible. Furthermore, it should be evident to the person skilled in the art that the method described in not intended to be necessarily limiting and may be practiced by the person skilled in the art in numerous other ways, for example, by adding steps, removing steps, skipping steps, or any combination thereof.

At 900, optionally a physician implants DDD-ICD 606 into a chest of a patient. Optionally, ICD 606 is implanted in a stomach pouch. Optionally, the patient is carrying an existent ICD 606 from a previous implantation.

At 901, optionally the physician inserts IPG 608 into the patient's chest. Optionally, IPG 608 is an OPTIMIZER III IPG for CHF by Impulse Dynamics Ltd.

At 902, optionally the physician inserts implantable lead connector 600 into the patient's chest and removably attaches the connector to ICD 606. Optionally, connector 600 is removably attached to IPG 608, or is integral with the IPG.

At 903, the physician connects RA cable 610A and RV cable 610B from ICD 606 to ports RA1 and RV1 in connector 600, respectively.

At 904, the physician connects RA cable 612A and RV cable 612B from IPG 608 to ports RA2 and RV2 in connector 600, respectively.

At 905, the physician connects an LS cardiac lead 612C from IPG 608 to the right ventricular septum in the patient's heart.

At 906, optionally the physician connects an RV cardiac lead 614A and an RA cardiac lead 614C to ports RV3 and RA3 in connector 600, respectively. Optionally, the physician connects shock electrode 610C from ICD 606 to RV cardiac lead 614A. Optionally, the physician inserts RV cardiac lead 614A into the right ventricle in the patient's heart. Optionally, the physician inserts RA cardiac lead 614C into the right atrium of the patient's heart. Before or after implantation the IPG and/or ICD are optionally programmed to operate together, for example, by programming a blanking period into the IPG according to the ICD used.

Figure 10:
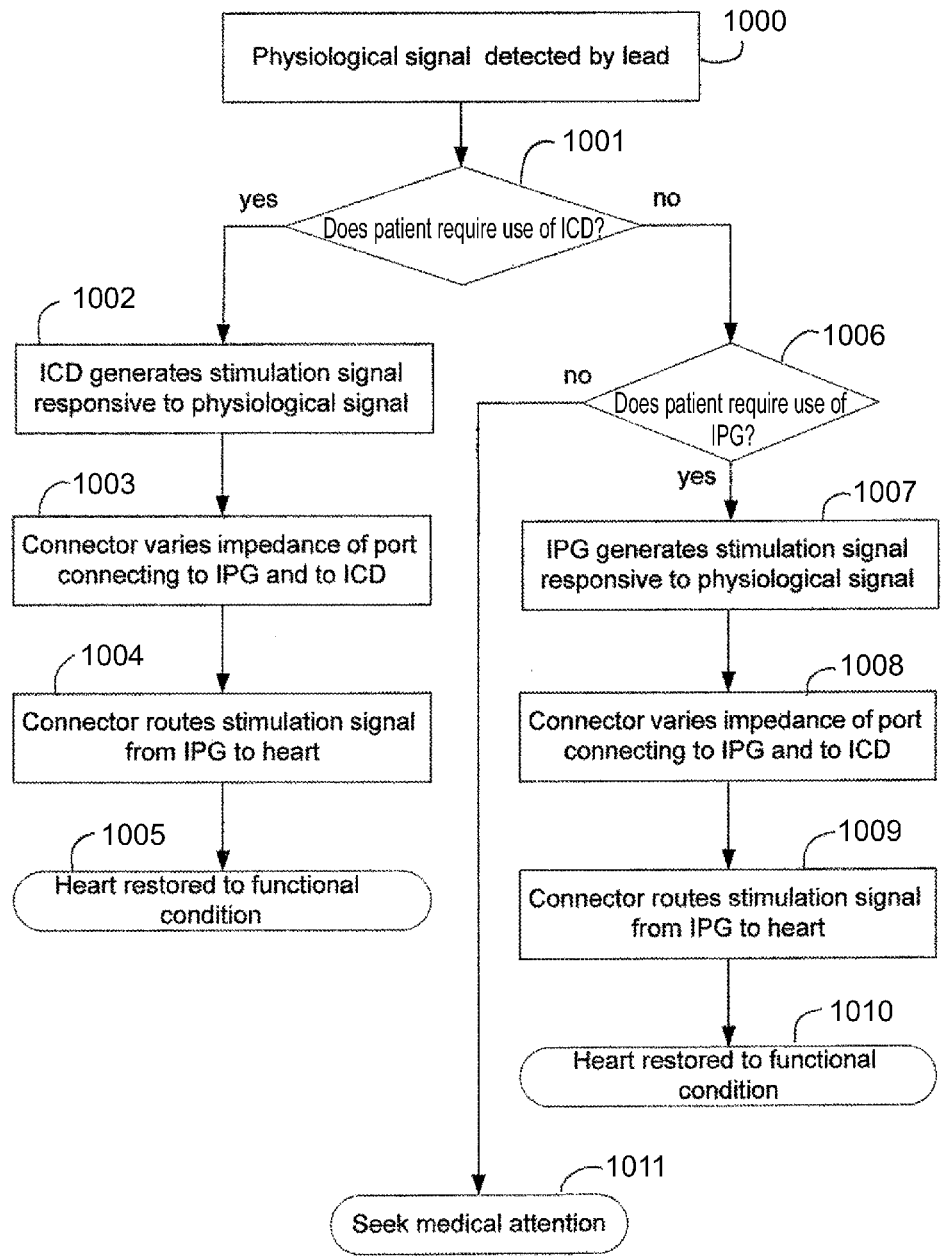
FIG. 10 illustrates a flow chart of a method of operation of an implantable lead connector interconnecting an IPG and an ICD including a pacemaker.

Reference is made to FIG. 10 illustrates a flow chart of a method of operation of an implantable lead connector interconnecting an IPG and an ICD including a pacemaker.

The exemplary method is described below with reference to the exemplary configuration previously described and shown in FIG. 9 for interconnecting multiple active implantable medical devices. It should be evident to a person skilled in the art that numerous other configurations for interconnecting a plurality of active implantable medical devices are possible. Furthermore, it should be evident to the person skilled in the art that the method described, as applies to the operation of the implantable lead connector, is not intended to be necessarily limiting and may be practiced by the person skilled in the art in numerous other ways, for example, by adding steps, removing steps, skipping steps, or any combination thereof.

At 1000, RV cardiac lead 614A and RA cardiac lead 614C sense physiological signals in the patient's heart. The RA signals and RV signals are transferred through connector 600 to ICD 606 and IPG 608. Optionally, the physiological signal is sensed by only one of the devices, and is picked up from the first device by the second device for example, IPG 606 from ICD 608. The port impedances in connector 600 are low. Optionally, only the port impedance of the device receiving the physiological signal is low, the port impedance of the second device is high. Optionally, controller 600 decides which device will sense the physiological signal. Optionally, controller 600 decides which device will analyze the signal. Optionally, the decision is based on a predetermined criteria preprogrammed into the connector.

At 1001, abnormal physiological signals are sensed by ICD 606. Optionally, the physiological signals are sensed by IPG 608. An analysis of the abnormal signals is made by ICD 606 for determining whether a stimulation signal is required for pacing or defibrillation. If an ICD generated stimulation signal is required continue to 1002. If the abnormal signals are not associated with a pacing or defibrillation problem, continue to 1006.

At 1002, optionally ICD 606 generates a stimulation signal.

At 1003, optionally connector 600, responsive to the detection of the stimulation signal from ICD 606, adjusts the impedances at ports RV2 and RA2 to high, essentially switching "off" IPG 608. Impedances at ports RA1 and RV1 are low so that ICD 606 is switched "on".

At 1004, optionally a defibrillation stimulation signal from ICD 606 flows through shock electrode 610C to RV cardiac lead 614A. Optionally, a pacing stimulation signal from ICD 606 flows through RA cable 610A and RV cable 610B into connector 600 and flow out the connector to heart 616 through RV cardiac lead 614A RA cardiac lead 614C.

At 1005, optionally heart returns to normal functioning. Return to 1000 for continuing to monitor the normally functioning heart.

At 1006, optionally, an analysis of the abnormal signals is made by IPG 608 for determining whether a stimulation signal is required for CHF. If an IPG generated stimulation signal is required continue to 1007. If the abnormal signals are not associated with a CHF problem, continue to 1011.

At 1007, optionally IPG 608 generates a stimulation signal.

At 1008, optionally connector 600, responsive to the detection of the stimulation signal from IPG 608, adjusts the impedances at ports RV1 and RA1 connecting to ICD 606 to high. Optionally, ICD 606 is essentially cut off from the circuit. Impedances at ports RA2 and RV2 in connector 600 connecting to IPG 608 are low.

At 1009, optionally a stimulation signal from IPG 608 flows through LS cardiac lead 612C to heart 616. Optionally, the stimulation signal from IPG 608 flows through RA cable 612A and RV cable 612B into connector 600 and flow out the connector to heart 616 through RV cardiac lead 614A and RA cardiac lead 614C.

At 1010, optionally heart returns to normal functioning. Return to 1000 for continuing to monitor the normally functioning heart.

At 1011, optionally seek urgent medical attention if the patient does not feel well.

Figure 11A:
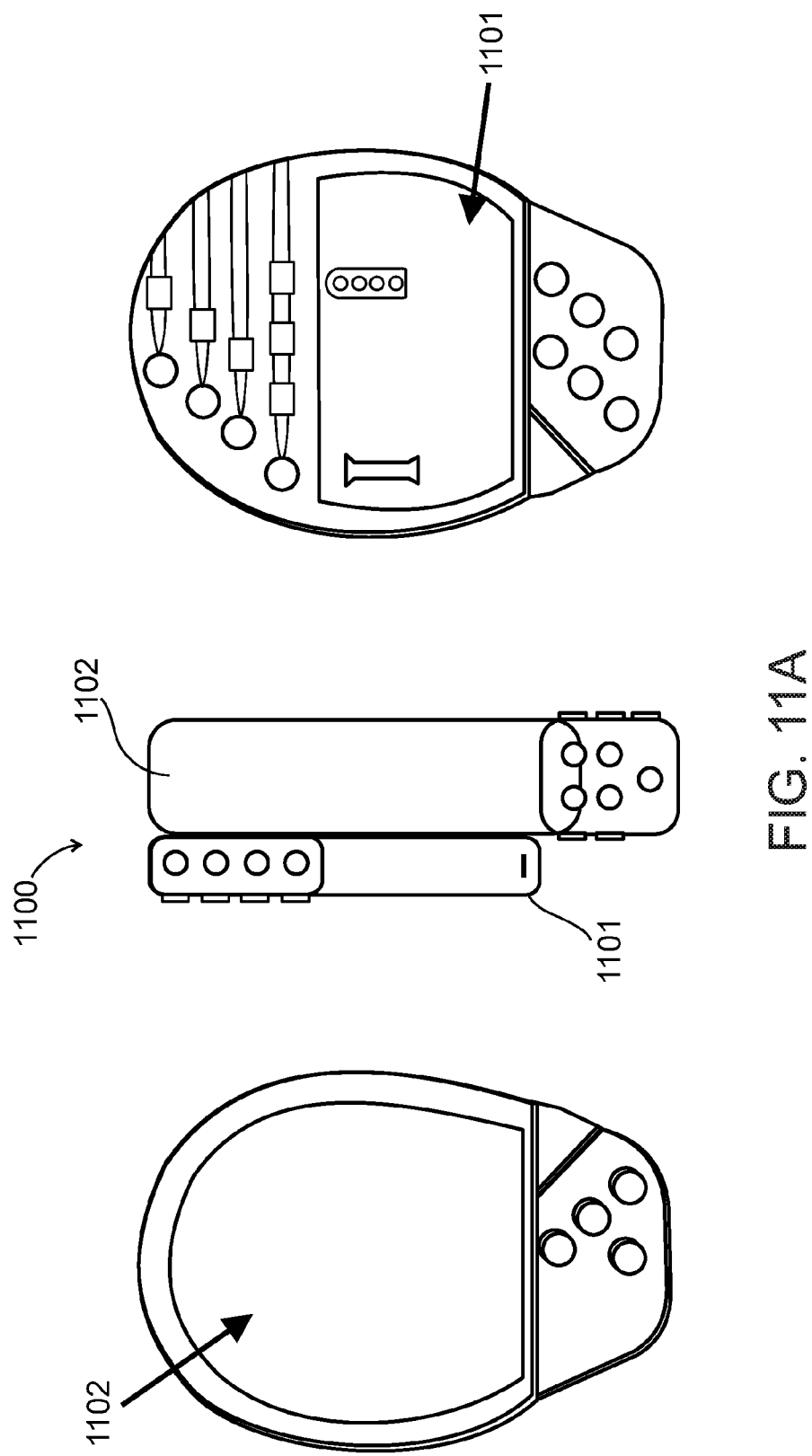
FIGS. 11A-11C schematically illustrate a combined IPG/ICD device including an attachable implantable lead connector, according to some embodiments of the present invention.
Figure 11B:
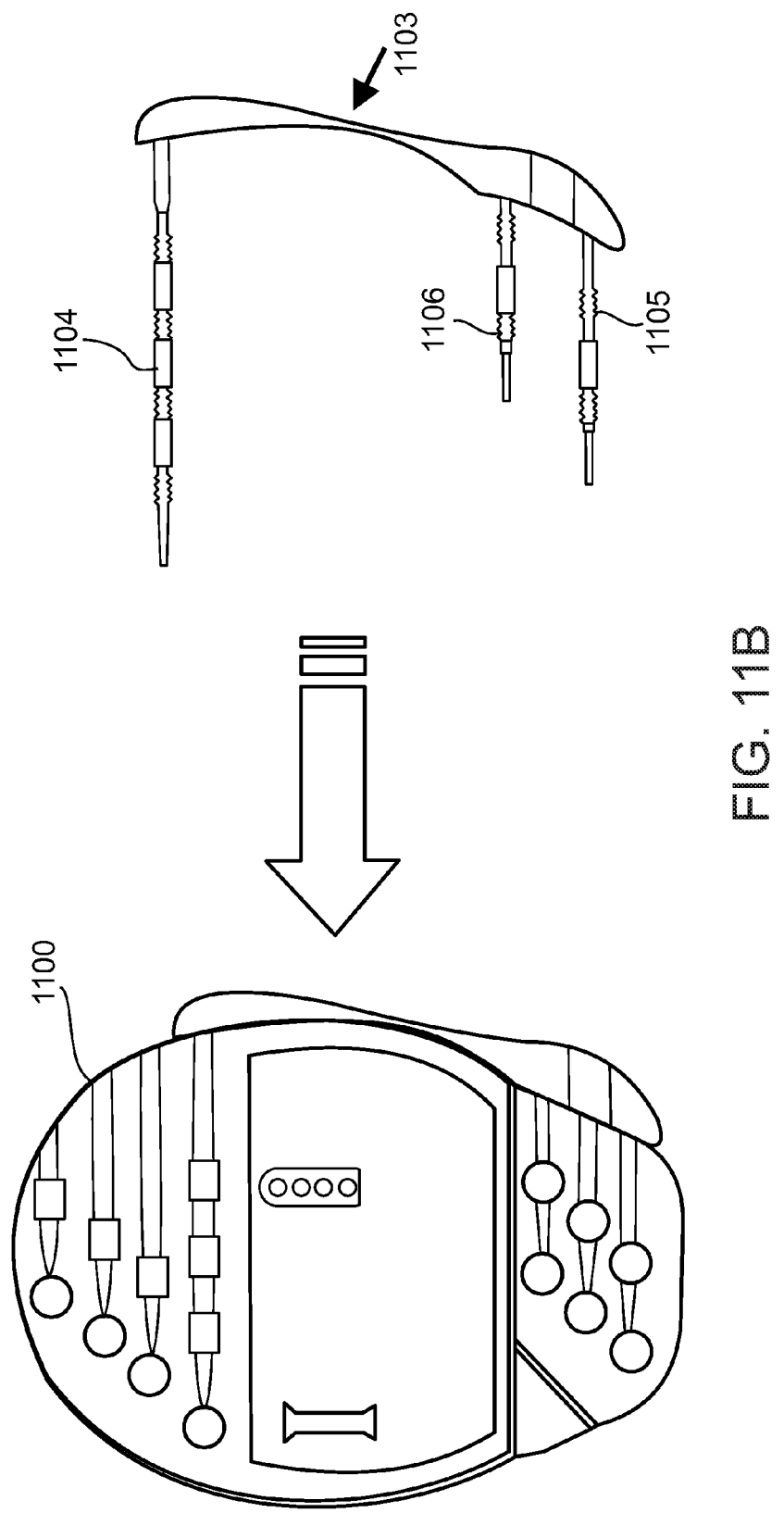
Figure 11C:
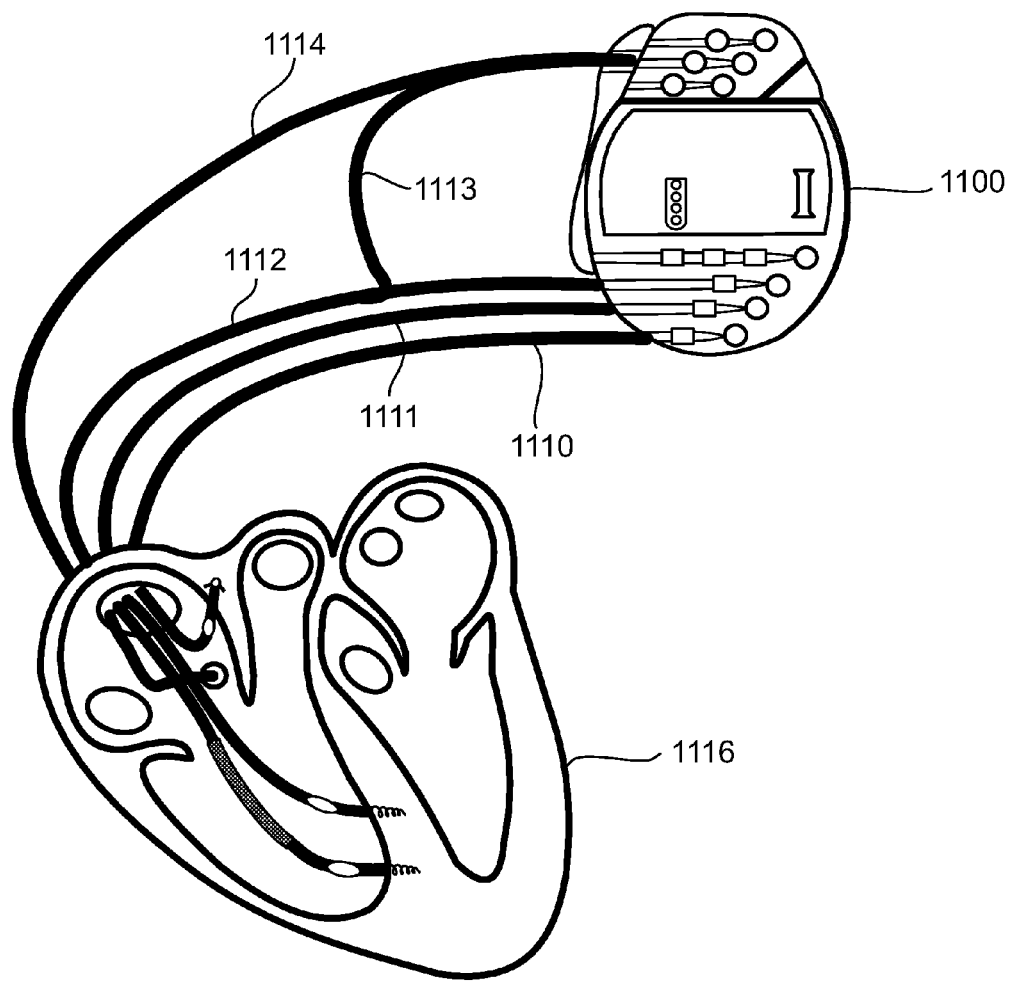

Reference is now made to FIGS. 11A-11C which schematically illustrate a combined IPG/ICD device 1100 including an attachable lead connector 1103, according to some embodiments of the present invention. In an exemplary embodiment of the invention, the interconnection circuitry described above is integrated with IPG device 1100 and element 1103 serves only to connect the ICD to the IPG. Optionally, connector 1103 is provided in kit form, optionally packaged with the IPG and/or in different sizes/designs for different ICD, for connecting an ICD to the integrated IPG/connection circuitry.

In an exemplary embodiment, IPG/ICD device 1100 comprises an assembly fitting together three removably attachable units IPG 1101, ICD 1102 and the lead connector 1103, or a plain connector 1103, if, for example, the connection circuitry is integrated with the IPG. Optionally, IPG 1101 is connected to connector 1103 through a DF-4 standard in-line tetrapolar connector 1104, which is optionally integral with 1103. ICD is connected to connector 1103 through an RV (right ventricular) IS-1 type connector 1105 and through an RA (right atrium) IS-1 type connector 1106, each of which are optionally integral with connector 1103 so that all ICD leads are shared with IPG 1101 through the connector. Single leads for connecting to a heart 1116 are optionally connected to the IPG ports, and include an RA lead 1110, a CCM lead 1111, an RV lead 112 to which is connected a shock lead 1113, and an optional LV (left ventricular) lead 1114.

Optionally the IPG and ICD are attached together. Optionally, the connector 1103 provides mechanical attachment, for example, using a bag or net (not shown), or an adhesive layer.

In some exemplary embodiments, lead connector 1103, IPG 1101 and ICD 1102 are similar to that shown in FIG. 1 at 100, 108 and 106, or reference 100 is integrated into IPG 1101. In another embodiment, lead connector 1103, IPG 1101 and ICD 1102 are similar to that shown in FIG. 2 at 200, 208 and 206, or reference 200 is integrated into IPG 1101. In another embodiment, lead connector 1103, IPG 1101 and ICD 1102 are similar to that shown in FIG. 3 at 300, 308 and 306, or reference 300 is integrated into IPG 1101. In lead connector 100, switching "on" and "off" of the device ports is done, in some exemplary embodiments, using a current limiting circuit. In lead connector 200, switching "on" and "off" of the device ports is done, in some exemplary embodiments, using serially connected voltage-dependent impedance elements. In lead connector 300, switching "on" and "off" of the device ports is done, in some exemplary embodiments, using serially connected voltage-dependent impedance elements and parallel connected voltage-dependent impedances.

Figure 12:
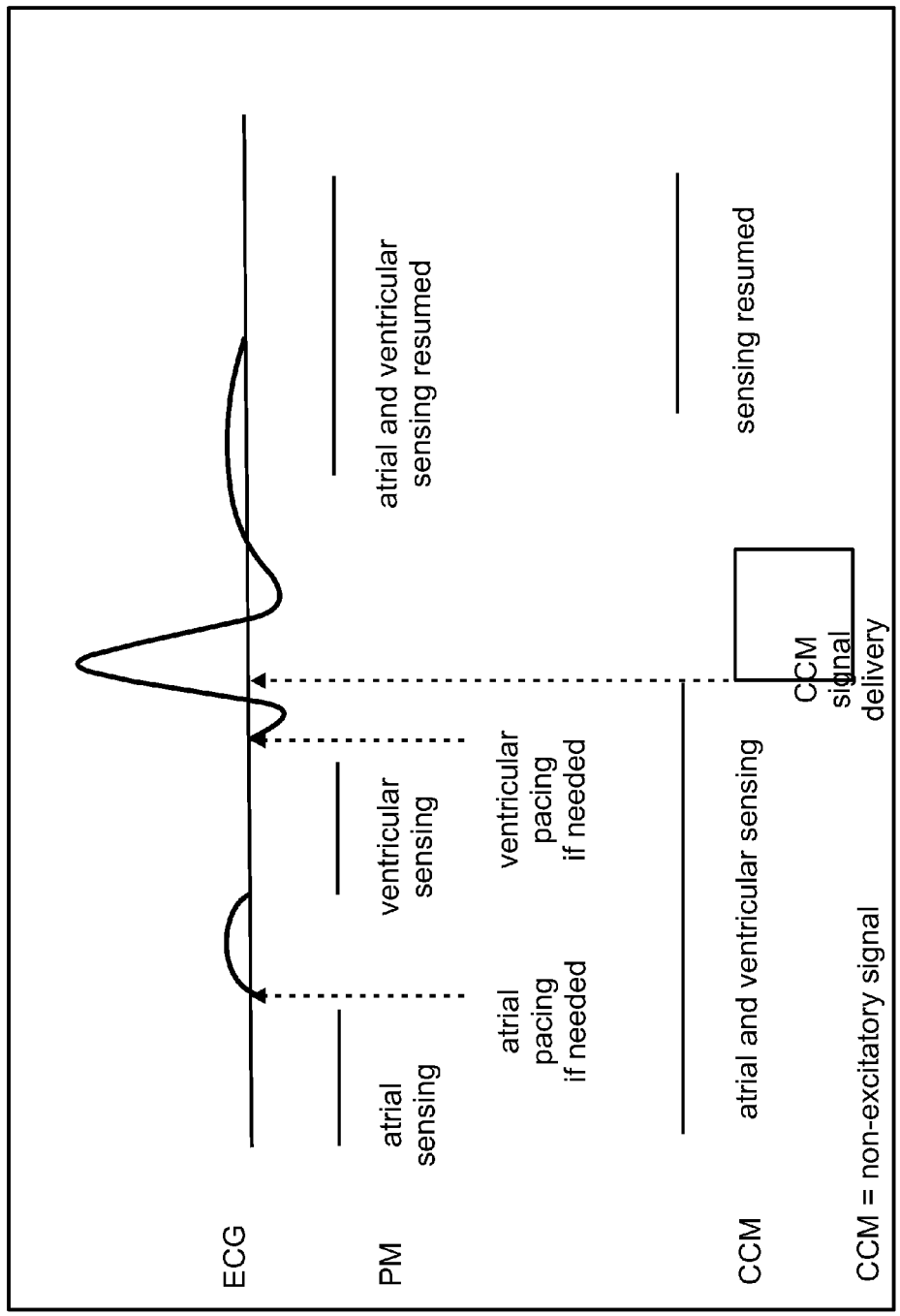
FIG. 12 shows an exemplary timing diagram, according to some embodiments of the present invention.

FIG. 12 shows an exemplary timing diagram. Typically, when a device uses the same electrode in order to sense tissue electrical activity (for example, in the range of miliVolts) it includes very sensitive sense amplifiers at the front-end connection to the electrode. When the device stimulates the muscle, it applies signals in the range of Volts. If the same electrode is used both for sensing and for signal delivery, then a blanking period may be used in which the device disconnects the sense amplifier from the electrodes while stimulation signal is delivered. If the delivered signal is relatively strong, a balancing phase is optionally added after the signal has been delivered in order to reduce the polarization of the electrode (due to the delivered signal) before reconnecting the sense amplifiers.

Optionally usage of a blanking period allows the same electrode to have multiple uses, provided that these are time separated.

Referring back to FIG. 12, the atrial sensing is operating, and if an atrial pacing is delivered, a blanking period applies to the atrial sense amplifier of the pacemaker. Similarly, following the activation of the ventricles a blanking period can be applied to the ventricular sense amplifier (if one or more of the ventricles was paced, or even if it was only a natural ventricular activity which was sensed).

Optionally, when two stimulation devices are connected to the same electrode, a similar logic can be applied if the timing of events do not overlap, and if the sense amplifiers of one device can be either blanked or tolerate the signal when the other device delivers its signal.

In an exemplary embodiment of the invention, the non-excitatory signal (CCM) can be delivered during the absolute refractory period, in a time when the sense amplifiers of the pacemaker (or ICD) can be blanked (e.g., by the devices or by the connector described herein). In an exemplary embodiment of the present invention a standard pacemaker or an ICD can be used without modification, and optionally programmed to have the blanking period long enough during the refractory period such as to avoid interference from the CCM signal.

In an exemplary embodiment of the invention, when the pacemaker applies a pacing signal, the sense amplifiers of the CCM delivery device are optionally blanked (e.g., if a preceding indication of pacing is obtained or using the above described connector), or designed to tolerate it. Optionally, such toleration can be either by the circuitry of the CCM delivery device, or by a circuitry in the lead connector that is connected to both devices and to the lead, and which may block most of the applied voltage.

The following patents and patent applications describe devices and methods which may be used for electrical stimulation and control, for example, as described herein and coupled to a connector or integral with interconnection circuitry. The following patents and applications are incorporated herein by reference in their entirety.

U.S. Pat. Nos. 6,317,631; 6,363,279; 6,330,476; 7,062,318; 7,167,748; 6,233,484; 6,236,887; 6,415,178; 7,218,963; 6,298,268; 6,463,324; 7,412,289; 7,460,907; 6,292,693; 6,675,043; 6,725,093; 7,310,555; 6,587,721; 6,442,424; 6,304,777; 6,285,906; 6,662,055; 6,522,904; 6,254,610; 6,152,882; 6,360,126; 6,223,072; 6,459,928; 6,233,487; 6,597,952; 6,360,123; 6,263,242; 6,424,866; 6,370,430; 6,292,704; 7,190,997; 7,171,263; 7,092,753; 6,348,045; 6,335,538; 6,529,778; 7,187,970; 6,993,385; 7,647,102; 7,027,863; 6,480,737; 6,602,183; 6,973,347; 6,749,600; 7,195,637; 6,571,127; 7,221,978; 6,947,792; 7,120,497; 7,006,871; 6,600,953; 6,993,391; 7,512,442; 7,437,195; 7,330,753; 7,502,649;

Ser. Nos. 10/039,845; 11/550,560; 11/931,724; 11/931,889; 11/932,064; 11/932,149; 11/933,168; 09/980,748; 10/116,

201; 11/673,812; 10/111,512; 11/247,736; 10/549,216; 12/155,448; 11/792,811; 11/919,491; 11/802,685; 11/991,481; 12/223,651; 11/736,183; 11/932,881; 11/932,812; 11/932,963; 11/318,845; 10/237,263; 10/526,708; 10/804,560; 10/570,576; 11/848,555; 11/573,722; 11/336,099; 10/599,015; 11/884,389; 11/816,574; 12/160616; 11/566,775; 11/551,282; 12/010,396.

Examples

Reference is now made to the following examples, which together with the above descriptions, illustrate some embodiments of the invention in a non limiting fashion.

In an exemplary embodiment of the invention, the interconnection circuitry is integrated with an IPG (such as a contractility modulation device, for example as describe din some of the above patents and applications). In one example, the circuitry is provided inside the casing of the IPG. In another example, the IPG includes a connector block and this block (e.g., of injected plastic) includes both connectors for attachment to an ICD or other device, such as pacemaker or combined CRT-ICD and connector(s) for one or more lead to the heart. Optionally the circuitry is also located within the connector block. In an exemplary embodiment of the invention the IPG and the interconnection circuitry are provided to a user for implantation as a monolithic inseparable device, in a sterile packaging, optionally with no space between the IPG and circuitry for bacterial growth. Optionally any integration is at a factory.

Optionally or alternatively, the interconnection circuitry is coupled using a rigid coupling or adhesive to the IPG. In another embodiment, the connection circuitry is coupled with a lead to the heart and/or leads suitable for connection to stimulator devices.

In an exemplary embodiment of the invention, the connector includes reed switches, dip switches or other configurations means which adapt the port mapping between inputs and outputs to match various configuration of attached devices. Optionally or alternatively configuration is determined by attachment to particular ports of the connector. Optionally unused ports are plugged. Optionally suitable plugs are provided with a kit of the IPG and/or connector. Optionally such a kit includes a rigid connector for interconnecting an ICD (or other device) and the IPG. Optionally such rigid connector also provides electrical connection. Optionally or alternatively, configuration is by attaching shorting sections between ports on the lead connector.

In an exemplary embodiment of the invention the connector includes two sets of inputs, each of between 1 and 4 inputs. In some cases, the inputs share a single cable connection. In another example, one or more splitters or combiners are used to match an existing lead cable to the lead connector.

In an exemplary embodiment of the invention the connector includes enough ports to accommodate all connections to/from the devices. Optionally or alternatively a plurality of connectors may be used. Optionally one connector can be a slave of another connector in that its internal impedance can be linked to a voltage on the other connector, for example, by electrical connection. In another example, a single monolithic connector is replaced by a plurality of connectors which are attached to each other by electrically conducting cables. Optionally or alternatively one or more isolators are provided as separate elements, for example, as a isolator device with two connections to a cable and a sensing cable terminating in a sensing element that is mounted on a lead (e.g., a coil sensor), whose sensing is used to control an isolation provided by the isolator. Optionally or alternatively the connector is flexible/bendable.

While in exemplary embodiments of the invention the integration circuitry isolates the IPG from the ICD (or other devices), in some embodiments, at least one of the devices or sensor inputs thereof is designed to withstand high voltages in sensor inputs rather than be isolated. Optionally, the interconnection circuitry comprises a short circuit or other fixed impedance connection between two or more inputs.

In an exemplary embodiment of the invention a coil sensor is used to allow an IPG to "sense" an impulse generated by a pacemaker or ICD. Optionally the coil is and/or an impedance matcher coupled thereto are configured so that the sensor input level is as expected. Optionally the connector generates one or more signals which emulate normal or abnormal beating of a heart, to feed faxed sensed signals into one of the devices.

In an exemplary embodiment of the invention, the connection circuit draws power from an IPG battery, for example, if they share a same casing or mechanical structure.

In should be noted that a feature of some embodiments of the invention is that an IPG circuitry need not be redesigned to work with a different stimulator. Optionally even a logic thereof is not changed and tested. Optionally some programming, such as changing blanking periods may be useful, but can be within normal ranges.

In should be noted that a feature of some embodiments of the invention is that all standard connectors remain as before. In particular, the cable connections to the ICD and/or connector of the cardiac lead can remain as before. Optionally the lead connector has a female socket to match the male plug of the cardiac lead and/or two male plugs to receive leads from the ICD. In an alternative embodiment, all ports are female and a special connector, using standard connector design, is used to couple the devices. Optionally or alternatively the connector includes integral leads to connect to the devices.

Following are some exemplary uses of and/or usage parameters for the above described pulse generators and connectors for treating heart or other organs, in accordance with exemplary embodiments of the invention.

In an exemplary embodiment of the invention, an electric field (e.g., energy) is delivered to a tissue during the refractory period of the tissue (or adjacent/related tissue) to affect tissue behavior. In an exemplary embodiment of the invention the electric field is delivered to a tissue to affect one or more of contraction force, structure, function, metabolism, secretion, biochemical process, gene expression, protein expression and/or protein phosphorylation of that tissue. Optionally the electric field is delivered to a tissue during the refractory period of the tissue to affect one or more of contraction force, metabolism, secretion, biochemical process, gene expression, protein expression, and protein phosphorylation of that tissue.

In some embodiments, the electric field is formed as an extended pacing pulse, having energy extended into the refractory period being suitable to obtain the desired effect. In an exemplary embodiment of the invention, the electric field is delivered in response to detection of activity of the tissue. Optionally the detected activity is a sensed electrical activity. Optionally or alternatively the detected activity is a sensed mechanical activity. Optionally or alternatively the field is applied immediately in response to the detected activity. Optionally or alternatively the field is applied at a delay from the detected activity, for example, at least 5 msec, 10 msec, 20 msec, 30 msec, 50 msec, 70 msec, 100 msec, or intermediate values and/or less than 150 msec (milliseconds).

In an exemplary embodiment of the invention the electric field is applied in response to indication that a pacing signal has been delivered to the tissue. Optionally the indication is received from a pacemaker. Optionally or alternatively the indication is obtained by sensing an electrical artifact generated by the pacing signal. Optionally or alternatively the indication is obtained by direct connectivity of the field generator to the pacing generator. Optionally or alternatively the field is applied to extend from (e.g., in continuation to) the pacing signal (e.g., immediately in response to the pacing indication). Optionally or alternatively the field is applied at a delay from an indication of pacing, of, for example, at least 5 msec, 10 msec, 20 msec, 30 msec, 50 msec, 70 msec, 100 msec or intermediate values and/or less than 150 msec.

In an exemplary embodiment of the invention the electric field comprises at least one monophasic field applied during the refractory period. Optionally the at least one monophasic field is alternating among heart beats between a negative field and a positive field. Optionally or alternatively the alternating occurs every few heart beats. Optionally or alternatively the alternating occurs after every heart beat. Optionally or alternatively the at least monophasic field has a trailing balancing phase to reduce charge accumulation on the electrode (reduce polarization). Optionally the balancing phase has an opposite polarity of that of the field with substantially smaller amplitude. Optionally or alternatively the balancing phase has a substantially zero amplitude.

In an exemplary embodiment of the invention the at least one monophasic field has a duration of at least 5 msec, 10 msec, 20 msec, 30 msec, 50 msec in each heart beat. Optionally or alternatively the at least one monophasic field has a duration which is not greater than 100 msec, 150 msec in each heart beat.

In an exemplary embodiment of the invention the field comprises a train of monophasic pulses. Optionally the overall length of the train from the beginning of the first pulse to the end of the last pulse is at of at least 5 msec, 10 msec, 20 msec, 30 msec, 50 msec or intermediate values in each heart beat. Optionally or alternatively the overall length of the train from the beginning of the first pulse to the end of the last pulse is not greater than 100 msec, 150 msec or intermediate values in each heart beat. Optionally or alternatively cumulative length of the monophasic pulses in the train is at of at least 5 msec, 10 msec, 20 msec, 30 msec, 50 msec or intermediate values in each heart beat. Optionally or alternatively, the cumulative length of the monophasic pulses in the train is not greater than 100 msec, 150 msec or intermediate values in each heart beat. Optionally or alternatively the duration of each pulse of the pulse train is at least 0.5 msec, 1 msec, 2 msec, 4 msec, 8 msec or intermediate values. Optionally or alternatively, the cumulative number of monophasic pulses in the train is at least 2, 3, 5, 8, 10, 15, 20, 25, 35, 50, or intermediate values in each heart beat. Optionally or alternatively, the cumulative number of monophasic pulses in the train is no greater than 100 in each heart beat. Optionally or alternatively the delay between consecutive monophasic pulsed is at least 0, 0.5 msec, 1 msec, 2 msec, 5 msec, 10 msec, 15 msec or intermediate values.

In an exemplary embodiment of the invention the electric field comprises at least one biphasic field applied during the refractory period. Optionally the at least one biphasic field starts with a positive phase. Alternatively, the at least one biphasic field starts with a negative phase. Optionally or alternatively the at least one biphasic field has symmetry between the positive and negative phases. Alternatively, the at least one biphasic field has asymmetry between the positive and negative phases. Optionally one phase has an amplitude of at least 10% greater than the other phase. Optionally or alternatively one phase has a duration of at least 10% greater than the other phase.

In an exemplary embodiment of the invention the at least one biphasic field has a time delay between the first phase and the second phase. Optionally the time delay is of at least 0.5 msec, 1 msec, 2 msec or intermediate values. Optionally or alternatively the at least one biphasic field is alternating between a start positive field and a start negative field. Optionally or alternatively the at least one biphasic field has a trailing balancing phase to reduce charge accumulation on the electrode (e.g., to reduce polarization). Optionally the balancing phase has an opposite polarity of that of the last phase of the field with substantially smaller amplitude. Optionally the balancing phase has a substantially zero amplitude.

Optionally the at least one biphasic field has a duration of at least 3 msec, 5 msec, 10 msec, 20 msec, 30 msec, 50 msec or intermediate values, in each heart beat. Optionally or alternatively the at least one biphasic field has a duration which is not greater than 100 msec, 150 msec or intermediate values, in each heart beat.

Optionally the field comprises a train of biphasic pulses. Optionally the overall length of the train from the beginning of the first pulse to the end of the last pulse is at of at least 5 msec, 10 msec, 20 msec, 30 msec, 50 msec or intermediate values, in each heart beat. Optionally or alternatively the overall length of the train from the beginning of the first pulse to the end of the last pulse is not greater than 100 msec, 150 msec or intermediate values, in each heart beat. Optionally or alternatively the cumulative length of the biphasic pulses in the train is at of at least about 5 msec, 10 msec, 20 msec, 30 msec, 50 msec or intermediate values, in each heart beat. Optionally or alternatively, the cumulative length of the biphasic pulses in the train is not greater than 100 msec, 150 msec or intermediate values, in each heart beat. Optionally or alternatively the duration of each phase of the pulse train is at least about 0.5 msec, 1 msec, 2 msec, 4 msec, 5.5 msec, 8 msec, or intermediate values. Optionally or alternatively the cumulative number of biphasic pulses in the train is at least 2, 3, 5, 8, 10, 15, 20, 25, 35, 50 or intermediate values, in each heart beat. Optionally, the cumulative number of biphasic pulses in the train is no greater than 100 in each heart beat. Optionally or alternatively the delay between consecutive biphasic pulsed is at least 0, 0.5 msec, 1 msec, 2 msec, 5 msec, 10 msec, 15 msec or intermediate values.

In an exemplary embodiment of the invention the electric field comprises at least one biphasic field and at least one monophasic field applied during the refractory period.

In an exemplary embodiment of the invention the electric field comprises at least 2 pulses.

In an exemplary embodiment of the invention the electric field is applied concurrently through multiple electrodes.

In an exemplary embodiment of the invention, the electric field is applied through multiple electrodes wherein at least one of the electrodes delivers a subset of the pulses and at least another one of the electrodes delivers another subset of the pulses.

In an exemplary embodiment of the invention the electric field is applied through multiple electrodes wherein at least one of the electrodes delivers one part of the field and at least another one of the electrodes delivers a second part of the field. Optionally, one part of the field and second part of the field are not identical. Optionally or alternatively one part of the field and said second part of the field comprise different time fragments of the electric field.

In an exemplary embodiment of the invention, the electric field delivered in each heart beat has a total energy which is at least 5 times greater than that which is sufficient for obtaining pacing in that heart through the electrodes. Optionally the electric field delivered in each heart beat has a total energy which is at least 10 times greater than that which is sufficient for obtaining pacing in that heart through the electrodes. Optionally the electric field delivered in each heart beat has a total energy which is at least 30 times greater than that which is sufficient for obtaining pacing in that heart through the electrodes. Optionally the electric field delivered in each heart beat has a total energy which is at least 50 times greater than that which is sufficient for obtaining pacing in that heart through the electrodes.

Optionally the electric field delivered in each heart beat has a total energy which is not greater 1 Joule. Optionally the electric field delivered in each heart beat has a total energy which is not greater 50 mili-Joule. Optionally the electric field delivered in each heart beat has a total energy which is not greater 10 mili-Joule.

In an exemplary embodiment of the invention the amplitude of the field is between 2 Volts and 20 Volts. Optionally, the amplitude is between 3 Volts and 12 Volts.

In an exemplary embodiment of the invention, the electric field is chronically delivered through implantable electrodes for long term treatment. Optionally the electric field is applied through coated electrodes having resistance between 100 Ohm and 3000 Ohm and cumulative surface area of at least 2 mm^2. Optionally, the electric field is applied through coated electrodes having resistance between 250 Ohm and 2000 Ohm and cumulative surface area of at least 3 mm^2.

Optionally or alternatively the electric field is applied through electrodes having a coating by at least one of a fractal coating, iridium-oxide, titanium-nitride.

In an exemplary embodiment of the invention the electrodes are connected to a smooth muscle. Optionally the field is chronically applied through implantable electrodes. Optionally or alternatively the chronic application of the field is used to treat a disease (e.g., one of metabolic, hypertension, obesity, diabetes, gi-tract motility).

In an exemplary embodiment of the invention the electric field is applied to the heart (e.g., using electrodes connected to the heart). Optionally the chronic delivery of the electric field treats heart failure. Optionally or alternatively, the chronic delivery of the electric field elevates force of contraction. Optionally or alternatively, the chronic delivery of the electric field improves cardiac output. Optionally or alternatively, the chronic delivery of the electric field improves cardiac stroke volume. Optionally or alternatively, the chronic delivery of the electric filed improves cardiac ejection fraction. Optionally or alternatively the chronic delivery of the electric field improves patient heart-related clinical condition. Optionally or alternatively, the chronic delivery of the electric field promotes reverse remodeling of the diseased heart. Optionally or alternatively the chronic delivery of the electric field normalizes gene expression in the tissue of genes associated with the disease. Optionally or alternatively the chronic delivery of the electric field normalizes protein expression in the tissue of proteins associated with the disease. Optionally or alternatively the chronic delivery of the electric field improves protein function in the tissue of proteins associated with the disease. Optionally or alternatively, the electric field is applied at least to the right ventricle, left ventricle, the ventricular septum, or combination thereof. Optionally electric field is applied to at least 2 locations in the heart. Optionally or alternatively the electric field is applied through endocardial electrodes, epicardial electrodes, trans-venous electrodes or combinations thereof.

In an exemplary embodiment of the invention, the electric field is applied on demand. Optionally, the electric field is applied on demand based on a patient input. Optionally or alternatively the electric field is applied on demand based on a physiological input associated with stress. Optionally or alternatively the electric field is applied on demand based on a physiological input associated with rest.

In an exemplary embodiment of the invention the electric field is applied in accordance with a logic circuitry configured to determine that the electrical conduction of a heart beat is of at least one of (and/or which one it is): a normally conducting beat, a paced beat, an abnormal conducting beat, is a normal ventricular conduction, is a abnormal ventricular conduction, is a ventricular ectopic activity. Optionally the logic circuitry is configured to minimize electric field delivery in substantially abnormal ventricular conduction beats. Optionally or alternatively the logic circuitry is configured to avoid electric field delivery in abnormal ventricular conduction beats. Optionally or alternatively the logic circuitry is configured to adjust (or select from some sets of) at least one of the parameters of the field delivery selected from a group comprising amplitude, timing, delay duration, shape of the field, in accordance with said determining. Optionally or alternatively the logic circuitry determines the type of electrical conduction by receiving indication from a pacemaker and/or defibrillator. Optionally or alternatively, the logic circuitry determines the type of electrical conduction by sensing the electrical activity of the tissue. Optionally or alternatively, logic circuitry determines the type of electrical conduction by analyzing at least one of the timing and morphology of the local electrical activity as sensed by at least one implantable electrode. Optionally or alternatively, the logic circuitry determines the type of electrical conduction by analyzing at least one of the timing and morphology of the global electrical activity as sensed between an implantable electrode and the can of the implantable pulse generator.

In an exemplary embodiment of the invention the electric field is applied to at least 5% of the heart beats of a week. Optionally electric field is applied to at least 5% of the heart beats of a day. Optionally, the electric field is applied to at least 10% of the heart beats of a day. Optionally or alternatively, the electric field is applied intermittently over a period of several hours per day. Optionally or alternatively, electric field is applied during several hours of a day in accordance with a programmed schedule.

In an exemplary embodiment of the invention the electric field is delivered through at least some of the electrodes that have at least one other use. Optionally the electric field is delivered through at least some of the electrodes through which a sensing circuitry senses electrical activity of the tissue. Optionally or alternatively the electric field is delivered through at least some of the electrodes through which a pacemaker or a defibrillator senses electrical activity of the tissue. Optionally or alternatively the electric field is delivered through at least some of the electrodes through which a pacemaker or a defibrillator deliver pacing and/or defibrillating signals. Optionally or alternatively electrodes used for the delivery of the field are bipolar. Optionally or alternatively the connection of the electrodes to the electric field generator device and to the pacemaker or defibrillator device has a protection electrical circuitry that prevents the delivery of signals from one device to adversely interfere with the sensing circuitry of the other device.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system, comprising:
a first implantable device having its own power supply;
a second implantable device having its own power supply;
interconnecting circuitry electrically connecting said first and second implantable devices; and
at least one implantable energy source for powering at least one of said first and second implantable devices and said interconnecting circuitry;
wherein said system is configured to allow power sharing between at least two of said first and second implantable devices and said interconnecting circuitry; and
wherein all pathways between said first implantable device, said second implantable device, and said at least one implantable energy source consist essentially of electrical conductors.

2. A system according to claim 1, further including at least one lead connector, wherein said system is configured to allow power sharing between said lead connector and at least one of said first and second implantable devices.

3. A system according to claim 2, wherein said at least one lead connector is configured to allow one of said first and second implantable devices to be powered by another one of said first and second implantable devices.

4. A system according to claim 3, further including at least a third implantable device having its own power supply, wherein said at least one lead connector is configured to allow one of said implantable devices to power the other ones of said implantable devices.

5. A system according to claim 2, wherein said at least one lead connector is configured to power at least one of said first and second implantable devices.

6. A system according to claim 2, further including at least a third implantable device having its own power supply, wherein said at least one lead connector is configured to power each of said implantable devices.

7. A system according to claim 2, wherein said at least one lead connector includes a power supply configured for powering said first and second implantable devices.

8. A system according to claim 2, wherein said at least one lead connector includes a power supply configured for powering first and second implantable circuitry connected to said first and second implantable devices, respectively.

9. A system according to claim 2, wherein said at least one lead connector has its own power supply.

10. A system according to claim 1, wherein at least one of said power supplies of said first and second implantable devices includes a battery.

11. A system according to claim 10, wherein said battery is rechargeable.

12. A system according to claim 10, further comprising a power harvester circuit configured for charging said battery.

13. A system according to claim 12, wherein said power harvester circuit is configured to harvest power from at least one of a body in which at least one of said first and second implantable devices is implanted, a power transmitter external to the body, and stimulation signals transmitted to the body by at least one of said implantable devices.

14. A system according to claim 13, further comprising a power storage element configured for storing power harvested from the body.

15. The system of claim 1, wherein each of said first and second implantable devices is selected from a cardiac pacemaker, a defibrillator, a pacing defibrillator, and an implantable pulse generator (IPG) for CCM (Cardiac Contractility Modulation).

16. A system according to claim 1, wherein each of said first and second implantable devices includes a battery, and wherein said first implantable device is selectably powered by said battery of one of said first and second implantable devices.

17. A system according to claim 1, further including an implantable lead connector adapted to connect leads from said first and second implantable devices to a shared implantable lead, said shared implantable lead configured to be attached to at least one of a target tissue and a target organ.

18. A system according to claim 17, wherein said first and second implantable devices share a single lead configured to at least one of:
transmit a stimulation signal to a target tissue or organ;
sense signals from a target tissue or organ; and
deliver therapy to a target tissue or organ.

19. A system, comprising:
a housing containing a first implantable device including a CCM (Cardiac Contractility Modulation) device and a second implantable device selected from at least one of a pacemaker and a defibrillator, wherein each of said first and second implantable devices has its own power supply; and
interconnecting circuitry electrically connecting said first and second implantable devices; and
at least one implantable energy source for powering at least one of first and second implantable devices and said interconnecting circuitry;
wherein said system is configured to allow power sharing between at least two of said first and second implantable devices and said interconnecting circuitry; and
wherein all pathways between said first implantable device, said second implantable device, and said at least one implantable energy source consist essentially of electrical conductors.

20. A system according to claim 19 including at least one lead connector configured to connect at least one of said first and second implantable devices to a target tissue or organ;
wherein at least one of:
at least one of said first and second implantable devices includes a resource configured to be shared with said at least one lead connector; and
said at least one lead connector includes a resource configured to be shared with at least one of said first and second implantable devices.

21. The system of claim 20, wherein said resource is at least one of a controller, a memory, a single lead, a power source, and logic circuitry.

22. The system of to claim 20, wherein said at least one lead connector is removably attachable to at least one of said first and second implantable devices and is configured to share resources of said at least one of said first and second implantable devices.

23. The system of claim 20, wherein said at least one lead connector is configured to physically interface said first and second implantable devices.

24. A system according to claim 20, wherein said at least one lead connector is configured to allow said power sharing between said first and second implantable devices.

25. A system according to claim 20, further comprising circuitry in said second implantable device configured to at least one of sense operational commands of said first implantable device and estimate a state of tissue due to operation of said first implantable device.

26. A system according to claim 25, wherein said second implantable device is configured to delay its operation based on at least one of said sensed operational commands and said estimated tissue state.

27. A system according to claim 19, further comprising at least one lead connector configured to connect at least one of said first and second implantable devices to a target tissue or organ;
wherein said at least one lead connector is configured to update a functionality of at least one of said first and second implantable devices.

28. The system of claim 27, wherein said at least one lead connector is configured to add a functionality provided by one of said at least one lead connector to at least one of said first and second implantable devices.

29. The system of claim 28, wherein said added functionality includes at least one of advanced pacing logic and an additional pacemaker function.

30. The system of claim 28, wherein said added functionality includes implantable cardiac defibrillators (ICD).

31. The system of claim 28, wherein said at least one lead connector is configured to at least one of:
add blanking periods to protect at least one of said first and second implantable devices from another implantable device;
synchronize functions of at least one of said first and second implantable devices with at least another implantable device;
delay operation of a second of said implantable devices after the operation of a first implantable device;
act as a switch for signal flow between said first and second implantable devices to and from a target tissue or organ;
switch off one of said first and second implantable devices and listen to another of said first and second implantable devices of said system and switch on said one of said first and second implantable devices when required;
allow one of said first and second implantable devices to listen to another of said first and second implantable devices of said system;
allow one of said first and second implantable devices to use information related to pacing in a first mode having a first set of parameters to change to a second mode having a second set of parameters different from said first set of parameters;
allow one of said first and second implantable devices to use the information to change windows settings; and switch between at least one sensing input and one first signal output for sensing and stimulating two different tissues at different times.

32. A system according to claim 19, further including at least one lead connector, wherein said system is configured to allow power sharing between said lead connector and at least one of said first and second implantable devices.

33. A system according to claim 32, wherein said at least one lead connector is configured to allow one of said first and second implantable devices to be powered by another one of said first and second implantable devices.

34. A system according to claim 33, further including at least a third implantable device, wherein said at least one lead connector is configured to allow one of said implantable devices to power the other ones of said implantable devices.

35. A system according to claim 32, wherein said at least one lead connector is configured to power at least one of said first and second implantable devices.

36. A system according to claim 32, further including at least a third implantable device, wherein said at least one lead connector is configured to power each of said implantable devices.

37. A system according to claim 32, wherein said at least one lead connector includes a power supply configured for powering said first and second implantable devices.

38. A system according to claim 32, wherein said at least one lead connector includes a power supply configured for powering first and second implantable circuitry connected to said first and second implantable devices, respectively.

39. A system according to claim 19, wherein said power supply of at least one of said first and second implantable devices includes a battery.

40. A system according to claim 39, wherein said battery is rechargeable.

41. A system according to claim 39, further comprising a power harvester circuit configured for charging said battery.

42. A system according to claim 41, wherein said power harvester circuit is configured to harvest power from at least one of a body in which at least one of said first and second implantable devices is implanted, a power transmitter external to the body, and stimulation signals transmitted to the body by at least one of said implantable devices.

43. A system according to claim 42, further comprising a power storage element configured for storing power harvested from the body.

44. A system according to claim 19, wherein each of said first and second implantable devices includes a battery, and wherein said first implantable device is selectably powered by said battery of one of said first and second implantable devices.

45. A system, comprising:
a first implantable device having its own power supply;
a second implantable device having its own power supply;
interconnecting circuitry which allows power to be shared between at least two of said first and said second implantable devices and said interconnecting circuitry; and
at least one implantable energy source for powering at least one of said first and second implantable devices and said interconnecting circuitry
wherein all pathways between said first implantable device, said second implantable device, and said at least one implantable energy source consist essentially of electrical conductors.

46. A system according to claim 45, wherein said interconnecting circuitry comprises a battery to be used for said power sharing.

47. A system according to claim 45, wherein said interconnecting circuitry is powered by at least one of said first and second implantable devices.

48. A system according to claim 45, wherein said interconnecting circuitry selectively uses power from one of said power supply of said first implantable device and said power supply from said second implantable device.

49. A system according to claim 45, wherein at least one of said first and second implantable devices includes a resource configured to be shared by said at least one lead connector.

50. A system according to claim 45, wherein each of said first and second implantable devices includes a battery, and wherein said first implantable device is selectably powered by said battery of one of said first and second implantable devices.

* * * * *